(12) United States Patent
Faye et al.

(10) Patent No.: US 7,179,889 B2
(45) Date of Patent: Feb. 20, 2007

(54) **PROPIONICIN T1 POLYPEPTIDE, A BACTERIOCIN FROM *PROPIONIBACTERIUM THOENII***

(75) Inventors: Therese Faye, Fagierstrand (NO); Helge Holo, As (NO); Thor Langsrud, As (NO); Ingolf Nes, As (NO)

(73) Assignee: Provisage As, As (NO)

( * ) Notice: Subject to any disclaimer, the term of this patent is extended or adjusted under 35 U.S.C. 154(b) by 482 days.

(21) Appl. No.: 10/252,819

(22) Filed: Sep. 24, 2002

(65) Prior Publication Data

US 2003/0096365 A1 May 22, 2003

Related U.S. Application Data

(60) Provisional application No. 60/324,046, filed on Sep. 24, 2001.

(51) Int. Cl.
*C07K 1/00* (2006.01)
(52) U.S. Cl. ............... 530/350; 530/344; 530/412; 530/300; 435/7.1
(58) Field of Classification Search ............... 530/344, 530/350, 412, 300; 435/71.3
See application file for complete search history.

(56) References Cited

U.S. PATENT DOCUMENTS

| 5,639,659 | A | 6/1997 | Barefoot et al. |
| 5,981,473 | A | 11/1999 | Barefoot et al. |
| 6,207,210 | B1 | 3/2001 | Bender et al. |

OTHER PUBLICATIONS

Lyon et al., Isolation and Purification of Propionicin PLG-1, a Bacteriocin Produced by a Strain of *Propionibacterium thoenii*, Jan. 1993, Applied and Environmental Microbiology, vol. 59, pp. 83-88.*

Murley et al., Cloning and Characterization of the Haemocin Immunity Gene of *Haemophilus influenzae*, Mar. 1997, Journal of Bacteriology, vol. 179, pp. 1684-1689.*
Holo et al., Bacteriocins of propionic acid bacteria, 2002, Lait, vol. 82, pp. 59-68.*
Grinstead et al., Jenseniin G, a Heat-Stable Bacteriocin Produced by *Propionibacterium jensenii* P126, Jun. 1992, Applied and Environmental Microbiology, vol. 58, pp. 215-220.*
Guo et al., PNAS, vol. 101, No. 25, pp. 9205-9210, 2004.*
Wells, Biochemistry, vol. 29, pp. 8509-8517, 1990.*
Faye et al. "Biochemical and Genetic Characterization of Propionicin T1, a New Bacteriocin from *Propionibacterium thoenii*", Appl. and Environ. Microbiol. 60:4230-4236 (2000).
Decision on Appeal for *Ex parte Bandman*, Appeal No. 2004-2319, pp. 1-15 (BPAI 2005).
Ennahar et al. "Class IIa bacteriocins: Biosynthesis, structure and activity" FEMS Microbiol. Rev. 24:85-106 (2000).
Kaletta et al. "Nisin, a peptide antibiotic: Cloning and sequencing of the *nisA* gene and posttranslational processing of its peptide product" J. Bacteriol. 171:1597-1601 (1989).
Mulders et al. "Identification and characterization of the lantibiotic nisin Z, a natural nisin variant" Eur. J. Biochem. 201:581-584 (1991).
Nes et al. "Class II antimicrobial peptides from lactic acid bacteria" Biopolymers 55:50-61 (2000).
Zendo et al. "Identification of the Lantibiotic nisin Q, a new natural nisin variant produced by *Lactococcus lactis* 61-14 isolated from a river in Japan" Biosci. Biotechol. Biochem. 67:1616-1619 (2003).

* cited by examiner

*Primary Examiner*—Hope Robinson
(74) *Attorney, Agent, or Firm*—Nixon & Vanderhye P.C.

(57) ABSTRACT

Propionicin T1 has been isolated from *Propionibacterium thoenii* and both the genetic operon and the products encoded thereby have been characterized. The operon contains two genes: one that encodes propionicin T1 and an one that encodes ABC transporter which may be an immunity factor which increases resistance of *Propionibacterium thoenii* bacteria to propionicin T1. Processes for using and making these products are also provided.

5 Claims, 7 Drawing Sheets

Figure 3A

| Sequence | Position |
|---|---|
| TGACCTGCGCCCTGAGCCACTGATGGCGAATCGCACTGATGCCAGCCCCG | 50 |
| GCCCTCGGCATCAAGATCCCCGTCTCTACACTTCGGCCCGAACCCCTCAG | 100 |
| GACCTTGGTGGCGAACGTGGGGAAGGCGTGCCGGACGCCCCTACCCGATC | 150 |
| GGGTACACCTGCTACCCGATCGGGTAGACCTTCGCGGAAACGCTTGCGTG | 200 |
| AGCACCTCACCTTCCACCAAGATCGAACCCAAGCTCGAGCACTC<u>AAACCC</u> | 250 |

<div style="text-align:right">-35</div>

RBS
<u>A</u>TTCGGAGAATATCCTCTGACTGATTAGAAAGGCCCGCTCGATGAAGAAG   300
                            -10         M  K  K

ACCCTCCTGCGAAGTGGAACGATCGCACTGGCGACCGCGGCTGCATTTGG   350
 T  L  L  R  S  G  T  I  A  L  A  T  A  A  A  F  G

CGCATCATTGGCAGCCGCCCCATCTGCCATGGCCGTTCCTGGTGGTTGCA   400
  A  S  L  A  A  A  P  S  A  M  A  V  P  G  G  C
                               ↑

CGTACACAAGAAGCAATCGCGACGTCATCGGTACCTGCAAGACTGGAAGC   450
T  Y  T  R  S  N  R  D  V  I  G  T  C  K  T  G  S

GGCCAGTTCCGAATCCGACTTGACTGCAACAACGCTCCAGACAAAACTTC   500
  G  Q  F  R  I  R  L  D  C  N  N  A  P  D  K  T  S

AGTCTGGGCCAAGCCCAAGGTAATGGTGTCGGTTCACTGTCTTGTTGGTC   550
   V  W  A  K  P  K  V  M  V  S  V  H  C  L  V  G

AACCGAGGTCCATCTCGTTCGAGACCAAGTGAGTCGATAGAACTGATATC   600
Q  P  R  S  I  S  F  E  T  K

RBS
CTCAATCCTTGGAATTCACTGCCCTCAGGGCGAAGAAGGGAACCCCATGA   650
                                                  M

GACTCGCGGTCGACGGACTGACGGTGAGATACCGGAAGAGGGTCGCCGTC   700
R  L  A  V  D  G  L  T  V  R  Y  R  K  R  V  A  V

GACGCGGTGTCCTGGCGGCTTGATGAGGGCTTCCACGCGCTGCTGGGCCC   750
  D  A  V  S  W  R  L  D  E  G  F  H  A  L  L  <u>G</u>  <u>P</u>

CAACGGCGCGGGGAAGTCCTCACTGCTGCGCGCGATCGCCACCCTCCAGC   800
  <u>N</u>  <u>G</u>  <u>A</u>  <u>G</u>  <u>K</u>    S  L  L  R  A  I  A  T  L  Q
Walker A

Figure 3B

| | |
|---|---|
| CGACGGTTTCGGGAACCGTTGAGCTGGACGGACGCAGCGGAACCGAGATC<br> P  T  V  S  G  T  V  E  L  D  G  R  S  G  T  E  I | 850 |
| CGAGCCCATCTTGGCTACTGCCCCCAGGAGAACCTCGGCAGGTCCCGATT<br> R  A  H  L  G  Y  C  P  Q  E  N  L  G  R  S  R  F | 900 |
| CACCGTTCGCGAGCACCTGGCCTACATGTGCTGGTTGCACCGTATCCCCG<br> T  V  R  E  H  L  A  Y  M  C  W  L  H  R  I  P | 950 |
| ACTCCCGGGTCCCGTCCGAGGTGGACCGGGTCATTGAGCTGGTGGATCTG<br> D  S  R  V  P  S  E  V  D  R  V  I  E  L  V  D  L | 1000 |
| GCCGAGCGTGCCGACGACCGGATCTCCGCCCTGTCCGGAGGGATGCGCCG<br> A  E  R  A  D  D  R  I  S  A  <u>L  S  G  G  M  R  R</u><br>                                 Linker peptide | 1050 |
| GCGGGTCGGCATCGGTTCGGCGCTGGTGGGCCGGCCCTCACTGGTGATCC<br> <u>R  V  G  I  G</u>  <u>S  A  L  V  G  R  P  S  L  V  I</u><br>                            Walker B | 1100 |
| TCGACGAACCCTCGGCAGGGCTGGACGTCGCCCAACGGGAGGCGCTGTCC<br> <u>L  D</u>  E  P  S  A  G  L  D  V  A  Q  R  E  A  L  S | 1150 |
| TCGGTCCTGCAACGCGTCTCGGCCGAGGCGATCACCATCGTGTCGACCCA<br> S  V  L  Q  R  V  S  A  E  A  I  T  I  V  S  T  H | 1200 |
| CATCGTCGAGGACGTCCTGGACCACGCCGACACCCTGACCGTGATGAACC<br> I  V  E  D  V  L  D  H  A  D  T  L  T  V  M  N | 1250 |
| AGGCCCGATTCGCCCACAGCGGGGCCTTCGACGAGTTCGCCGGATCCCGC<br> Q  A  R  F  A  H  S  G  A  F  D  E  F  A  G  S  R | 1300 |
| GATCTGGAGGCCGTGCGCATCGCGCTACCTGGAGACGGTGACACCGTGAG<br> D  L  E  A  V  R  I  A  L  P  G  D  G  D  T  V  R | 1350 |
| GCACACGGGAGTCATGCTGTGGGCCCGTCACCACCGGGTGGGACCATCGG<br> H  T  G  V  M  L  W  A  R  H  H  R  V  G  P  S | 1400 |
| TCGCGGTGGCCGTCATCGCCTCGGCGGTCGTGCGCGGACTGGTGCTCCCC<br> V  A  V  A  V  I  A  S  A  V  V  R  G  L  V  L  P | 1450 |

Figure 3C

```
ATCAGCTCCGACGGAAGCGAGATCGAGGTGGCCCCACTGTGGATCGCCAC   1500
 I  S  S  D  G  S  E  I  E  V  A  P  L  W  I  A  T
CGTCTGTGTCGTCCCGTTGCTGTTCATGTTCACCACCGAGACCGACACCG   1550
 V  C  V  V  P  L  L  F  M  F  T  T  E  T  D  T
ACCGCACCGCCCCACGATCCCTGACGGCCCGCCGGTGGGCCCTGCTGGGC   1600
 D  R  T  A  P  R  S  L  T  A  R  R  W  A  L  L  G
ATCGCTGTCCTCACGAGCGCGGTCATCGCCCTGGCAGCCTTCCCCACCAC   1650
 I  A  V  L  T  S  A  V  I  A  L  A  A  F  P  T  T
CATCGGCGAATGGGGACTCATCGCCACCTGGCGCGACGCCGTCGCCCTGC   1700
 I  G  E  W  G  L  I  A  T  W  R  D  A  V  A  L
TCGGGCTGGGCCTGCTGAGCCTGGCCGTCCTGCCGCCGGCCGCCATCTGG   1750
 L  G  L  G  L  L  S  L  A  V  L  P  P  A  A  I  W
GTGGCCCCGCTGGTCGCGGCACTGGCATCGATGATGTTCAGCTGGCCGCT   1800
 V  A  P  L  V  A  A  L  A  S  M  M  F  S  W  P  L
GCACCCGGGGACTGTCCCTGGGACTGTGGGGAGCGCTGCGCGCCGCGGCC   1850
 H  P  G  T  V  P  G  T  V  G  S  A  A  R  R  G
GACCTGCTGCTGGACCCGGGCGTGACCGATCTGAGTATTCCGCTGTGCCT   1900
 R  P  A  A  G  P  G  R  D  R  S  E  Y  S  A  V  P
GCTGATCAGGGCGGCCGGTAGTCGTCTTCCTCGTCAACGGCCTGACATGG   1950
 A  D  Q  G  G  R
ACCCCACGCCCAASCGCCCCCGATGGGCGACCCCACCACCGCACCGTGAC   2000
GCCCCACCGCTCCAGTGCCCGGGCCGGCATCAGGAGAGCCTCCCTGGCCG   2050
TGCCGATGGCCTGCCTGGTCGCCGTCGTCTCGGCCTGGCCGTGGGTGACG   2100
TCACTGTCGTGGTGGGGCGGCAGCCCCAGGCTCCTGCTGGCCGGCGAGAT   2150
CCCCGCCTCGTTCTTCATCGCCATACCCTGCGCGGTACTGGCCGGCGTGG   2200
TGACAGGCCA                                           2250
```

Figure 4

```
ABC/1-429         1  ---IEVESVSKSEGRIRAEDNLSFSVAEGEIMGIIGHNGAGKTTAIREHIAGILHPDSGTVR
Homologous/1-429  1  ---LSIEESICKSYRHEAVKNMSFHVNENECVALLGPNGAGKTTTLQMEAGILSPTSGTIK
Putative/1-429    1  ---LAIDCINLRLYEGQITGLLGHNGAGKTTTMSILCGLYAPSSGTAKIYQRDIRTDLRRV
putative/1-429    1  ---ITIDRLEEKRYGDKTAVSDLSFEINPGKVIGFLGPNGAGKSTTMRMIVGIDAPTSGRAL
ABC-C/1-429       1  ------IDRAAVRDLNLNLYEGQIIVLLGHNGAGKTTTLSMLTGLFPPTSGRAY
ORF2/1-429        1  MRIAVDGLIVRYRKRVAVDAVSWRDEG-FHALLGPNGAGKSSLLRAIATLQPTVSGTVE ABC/1-429         59 VGGHDVTEDPESVKSMIGYLPEPNLVERFRAGDLLRYFGELYGMPRDVIEDRIAEILEL
Homologous/1-429  59 ILG---EKKIDRRL-LGYLPQYPAFYSWMTANEFLIEAGRLSKKCQEKIGEMLEF
Putative/1-429    59 RDVLG-ICPQHNMLFSHLTVSEQLRLEAALKGVPDSELTSQVDEILASVSLTEKANKLAS
putative/1-429    59 VGGKR-YEELRHPLREVGALLDARAGHPGRSARHHLLGLARSNGIPASRV---GEMIQT
ABC-C/1-429       49 ISGYEISODMVORKSLGLCPQHDILEDNEIVAEHLYFAQLKGISROKCPEEVKOMLHI
ORF2/1-429        60 IDG----RSGTETRAHLGYCPQENLGRSRFTVREHLAYMCWLHRIPDSRVPSEVDRVIEI ABC/1-429        119 VGMIDRAMDPINTFSKGERQRFGIARAIIHDPPLIIFDEPTMGLDPATAEFSIREEIRDLK
Homologous/1-429 114 VGIHEAAHKRIGGYSGGMKQRLGEAQALIHKPKFLLLDEPVSALDPTGRFEVLDMMREIK
Putative/1-429   118 TLSGGMKRRLCIGIAFIGGSREVILDEPTAGVDVTARKDIWKLIQRNKEGRTILSTHM
putative/1-429   114 VGISEVANKRIGSFSLGMQRLGIAALLGDPKVLLFDEPVNGLDPDGVRWVREIMRSLA
ABC-C/1-429      109 IGLEDWNSRSRFLSGGMRKLSIGIALLAGSKVLILDEPTSGMDAISRRAIWDLIORQK
ORF2/1-429       116 VDLAERADDRISALSGGMRRVGISALVGRPSEVILDEPSAGLDVAQREALSSVIQRVS ABC/1-429        179 GSKTMIECTHYMEEAEYICDRVAIINQGRILDIGTPDELKSKIRGDLVLEVKVRDISSVG
Homologous/1-429 174 KHMAVIFSTHIVHDAEQMCDQVVIMKNGEISWKGELQE------
Putative/1-429   178 DEADVAISDRIAILSQ------
putative/1-429   174 AEAGRTIFVSSHIMSEM--QETADHELVIGRGKIIADAPIEEVIAGSSLTAVRVRTP---
ABC-C/1-429      169 SDRTEVALTHFMDEALLGDRIAIMAKGEIOCCGS----
ORF2/1-429       176 AEAITIVSTHIVEDVLDHADITMNQARFAHSGAFDEFAGSRDLEAVRIALPGDGDTVR
```

PROPIONICIN T1 POLYPEPTIDE, A BACTERIOCIN FROM *PROPIONIBACTERIUM THOENII*

CROSS-REFERENCE TO RELATED APPLICATION

This application claims the benefit of provisional Appln. No. 60/324,046, filed Sep. 24, 2001.

BACKGROUND OF THE INVENTION

This invention relates to a novel bacteriocin and a putative immunity factor; they may be provided in polypeptide or nucleic acid form. Processes for using and making these products are also provided.

Bacteriocins are antibacterial peptides or proteins produced by a wide range of micro-organisms. Several of them have been isolated and characterized, and their mode of action have been determined (10–11, 16–17). They may be bacteriocidal or bacteriostatic. Of special interest are bacteriocins produced by food-grade organisms like lactic acid bacteria (e.g., *Lactococcus, Streptococcus, Pediococcus, Leuconostoc, Lactobacillus, Carnobacterium*) and propionic acid bacteria (e.g., *Propionibacterium*) because of their potential application in food preservation (29). Although a number of bacteriocins from gram-positive bacteria have broad spectrum inhibitory activity, most of the characterized bacteriocins have a relatively narrow spectrum of activity.

Antibacterial proteins produced by lactic acid bacteria have been isolated and characterized. For example, nisin is produced by strains of *Lactococcus lactis* and is approved as a food additive in many countries. The efficiency of nisin in preventing the growth of spoilage bacteria has been proven in a number of food systems (5). Another is pediocin PA1 produced by *Pediococcus acidilactici* PAC1.0 (6), which is very active against the food-borne pathogen *Listeria monocytogenes* (22), which is usually not very sensitive to nisin (30).

There are two major groups in the genus *Propionibacterium*: (i) the acnes group or cutaneous strains and (ii) the classical or dairy strains. The latter have a long history of use in dairy fermentation. These bacteria are especially important in starter cultures in the production of Swiss-type cheeses, where they are responsible for the formation of flavor, texture, and the characteristic eyes. Various MICRO-GARD™ MG products are produced by fermentation of skim milk with a *Propionibacterium freudenreichii* ssp. *shermanii* strain. This product inhibits molds, gram-negative species, and hetero-fermentative lactic acid bacteria. It is used as a preservative in about 30% of the cottage cheese made in the USA (3). A 700 dalton peptide has been implicated in its action, but it has not been unequivocally demonstrated that the active ingredient is a bacteriocin (7).

Among the dairy propionibacteria only two bacteriocins have been described, propionicin PLG-1 from *P. thoenii* P127 (13–14) and *jenseniin* G from *P. thoenii* P126 (formerly *P. jensenii*) (7, 24). Propionicin PLG-1 is active against a variety of micro-organisms like propionibacteria, as well as many gram-positive and gram-negative bacteria and even fungi (13). This bacteriocin has been purified to homogeneity and, according to amino acid composition analysis, it contains 99 amino acid residues and has a calculated molecular weight of 9328 (20). Propionicin PLG-1 is stable after long-term storage in dry or frozen state and kills rapidly sensitive cells upon exposure in culture medium or skim milk (9). Jenseniin G is a heat stable bacteriocin that inhibits several propionibacteria and lactic acid bacteria (24), like *Lactobacillus delbruecki* ssp. *bulgaricus* and *Streptococcus thermophilus*. This bacteriocin has therefore a potential role in preventing over-acidification of yogurt (31). See also U.S. Pat. Nos. 5,639,659 and 5,981,473. However, none of the bacteriocins from propionibacteria mentioned above have been thoroughly described, and their primary structures are not known.

Bacteriocin-producing starter cultures produce bacteriocins during fermentation of food products. The use of bacteriocin producers as starter cultures may therefore be of advantage in protecting fermented foods from transmission of food-borne pathogens as compared to starter cultures lacking bacteriocin. Secondary cultures containing a bacteriocin may also contribute to accelerated ripening of dairy products by killing microbes in the primary starter cultures. Dead bacteria will gradually lyse and release cell compounds like lipids, peptides, and amino acids important for the characteristics of the product. Bacteriocin-containing compositions are also applied to food surfaces in accordance with U.S. Pat. No. 6,207,210.

Several bacteriocin producers have already been isolated from foods. Therefore it is presumed that a mixture of different bacteriocins in variable amounts is already present in food products. Such bacteria and their products are generally regarded as safe (GRAS) since they have been an important part of the human diet for centuries. Microbes may be transfected with portions of the operon to produce the bacteriocin and/or the ABC transporter. One limitation to the use of bacteriocin producing propioni-bacteria is the slow growth and relatively late bacteriocin production. An alternative and more effective approach could be to use purified and concentrated bacteriocins directly as food additives.

If bacteriocins are going to be used in food manufacturing, there are some important requirements such as lack of toxicity, stability, broad activity spectrum, no effects on food properties, and a thorough understanding of their biochemical and genetic properties. Here, we describe a new bacteriocin from propionibacteria called propionicin T1. This is the first bacteriocin from propionibacteria to be characterized at the level of its amino acid and nucleotide sequences. A long-felt need to control the growth of microbes is addressed thereby. Other advantages and improvements are discussed below or would be apparent from the disclosure herein.

SUMMARY OF THE INVENTION

An objective of the invention is to provide a bacteriocin.

Another objective is to provide an ABC transporter which may be an immune factor for the bacteriocin. It may also serve as a coregulated marker for expression of the operon.

The bacteriocin has a nucleotide or amino acid sequence which is structurally identical to propionicin T1 and was originally isolated from *Propionibacterium thoenii*, or which has a similar chemical structure. The ABC transporter which is structurally identical to orf2 or a membrane protein with similar chemical structure may be an immune factor which increases resistance to the bacteriocin. Fusion polypeptides and chimeric nucleic acids have at least one sequence which is not derived from *Propionibacterium thoenii* (i.e., a heterologous domain or region, respectively). Compositions thereof may be used during food processing, as a preservative, or to treat an anaerobic infection (e.g., a pathogenic bacteria).

A shuttle vector having at least one ori region may be used to replicate a gene of the operon shown in FIGS. 3A–3C or a derivative thereof. An expression construct having at least one regulatory region may be used to transcribe a gene of the operon shown in FIGS. 3A–3C or a derivative thereof or to produce the polypeptide encoded by the gene or derivative thereof. The shuttle vector or expression construct may be transfected into a microbe. The transfected microbe may be used to produce the bacteriocin and/or ABC transporter. The protein may be isolated and optionally at least partially purified or purified to homogeneity. Compositions may be added to cultures before, during, or after fermentation; mixed with or applied to the surface of a food product; or applied topically to the skin. Alternatively, transfected microbes may be added to the culture before, during, or after fermentation. The bacteriocin or ABC transporter may be expressed by constituitive, inducible, or repressible regulatory regions.

Probes or primers may be used to identify genes or microbes, to hybridize with or replicate nucleic acids which are structurally related to propionicin T1 or its immune factor, and to detect their presence. Fragments of the polypeptide or nucleic acid may be used to produce fusion polypeptides or chimeric nucleic acids, to mimic or compete with native molecules, to produce specific binding molecules, or combinations thereof. Specific binding molecules for bacteriocin and ABC transporter may be used to detect these molecular markers and to identify propionibacteria by genotype or phenotype.

Also provided are processes for making and using these products, which may then be subjected to further processing. The bacteriocin or the ABC transporter may be obtained from a natural source (e.g., strains of propionibacteria), a reaction mixture with reagents and/or products (e.g., cell-free replication, transcription, and translation; manual or automated linkage of nucleotide or amino acid monomers), or genetically-engineered sources or cells (e.g., recombinant molecules, transfected microbes). The nucleic acid may be transfected into a microbe. A microbe containing bacteriocin may release it into the surroundings (e.g., fermentation culture, food product); immune factor increases resistance to the inhibitory activity of the bacteriocin. Here, we show that sensitive microbes were killed with the bacteriocin. Resistance may be increased or decreased by increasing or decreasing the expression of the ABC transporter.

Further embodiments of the invention will be apparent to a person skilled in the art from the following detailed description and claims, and generalizations thereto.

BRIEF DESCRIPTIONS OF THE DRAWINGS

FIG. 1 shows growth kinetics and bacteriocin production of *P. thoenii* 419. Bacteriocin activity was determined from cell-free culture supernatants using a micro-titer plate assay. Sensitive indicator was *P. acidipropionici* ATCC 4965. Symbols: ♦, OD at 620 nm; ■, BU/ml.

FIG. 2A shows growth of the sensitive indicator *P. acidipropionici* ATCC 4965 with (1000 BU/ml culture) and without propionicin T1. Symbols: ◇, without bacteriocin; ■, with bacteriocin. FIG. 2B shows the optical density (620 nm) of growing cultures of *P. acidipropionici* ATCC 4965 with and without propionicin T1. Symbols: ◇, without bacteriocin; ■, with 100 BU/ml culture; Δ, with 1000 BU/ml culture.

FIGS. 3A–3C show the sequence of 2210 contiguous nucleotides (SEQ ID NO:10) of the operon, including the open reading frames pctA and orf2. Potential −35 and −10 sites and RBS (bold) are indicated. The amino acid sequence of propionicin T1 (SEQ ID NO:11) showing the cleavage site of the leader sequence (↑) and the amino acid sequence of an ABC transporter (SEQ ID NO:12) showing three conserved sequence motifs in the ATP-hydrolyzing domain are also included.

FIG. 4 shows an alignment of prokaryotic and eukaryotic ABC transporters (SEQ ID NOS:13–17) and the N-terminal domain of a protein encoded by orf2 (SEQ ID NO:18).

DESCRIPTION OF SPECIFIC EMBODIMENTS OF THE INVENTION

Figure 1:
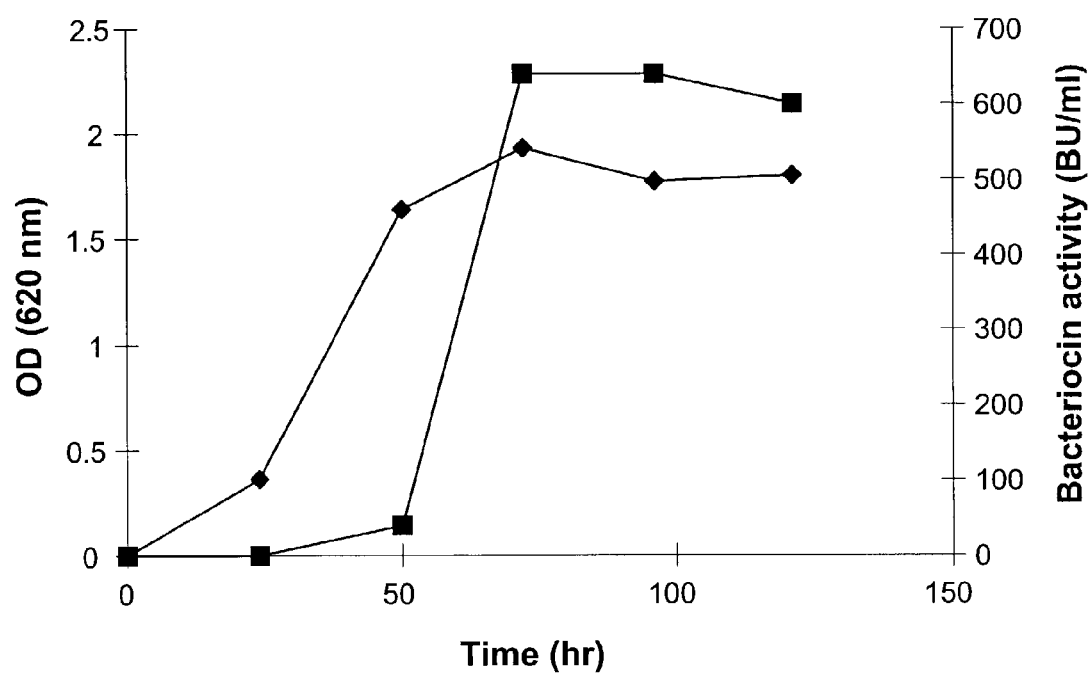

Nucleic acids corresponding to all or part of a pctA transcript or gene, which include mutants and other variants thereof, may be used to confer bacteriocin activity (e.g., in vivo or in vitro expression of bacteriocin polypeptide), to transfect a microbe or cell and thereby transfer such activity, to inhibit such activity, or to detect complementary polynucleotides. Similarly, polypeptides corresponding to a protein encoded by pctA, which include mutants and other variants thereof, may be used directly to provide bacteriocin activity if functional or compete with it if not; to select inhibitory antibodies, agonists, and antagonists; and to identify, isolate, or to detect interacting proteins (e.g., antibodies, receptor agonists or antagonists) by binding assays.

Nucleic acids corresponding to all or part of an orf2 transcript or gene, which include mutants and other variants thereof, may be used to confer ABC transporter activity (e.g., in vivo or in vitro expression of ABC transporter polypeptide), to transfect a microbe or cell and thereby transfer such activity, to inhibit such activity, or to detect complementary polynucleotides. Similarly, polypeptides corresponding to a protein encoded by orf2, which include mutants and other variants thereof, may be used directly to provide ABC transporter activity if functional or compete with it if not; to select inhibitory antibodies, agonists, and antagonists; and to identify, isolate, or to detect interacting proteins (e.g., antibodies, ligand agonists or antagonists) by binding assays.

Another aspect of the invention is a hybrid polynucleotide or polypeptide (e.g., a transcriptional chimera or a translational fusion). In transcriptional chimeras, at least a transcriptional regulatory region of a heterologous gene is ligated to a bacteriocin or ABC transporter gene or, alternatively, a transcriptional regulatory region of the operon is ligated to at least a heterologous polynucleotide. The reading frame of a bacteriocin or ABC transporter polypeptide and the reading frame of at least a heterologous amino acid domain are joined in register for a translational fusion. If a reporter or selectable marker is used as the heterologous region or domain, then the effect of mutating a nucleotide or amino acid sequence on protein function may be readily assayed.

"Bacteriocin" refers to pctA or a protein encoded thereby from a strain of propionibacteria, mutants and polymorphisms found in nature, and variant forms thereof (e g., mutants and polymorphisms not found in nature). The chemical structure of the bacteriocin may be a polymer of natural or non-natural nucleotides connected by natural or non-natural covalent linkages (i.e., polynucleotide) or a polymer of natural or non-natural amino acids connected by natural or non-natural covalent linkages (i.e., polypeptide).

See Tables 1–4 of WIPO Standard ST.25 (1998) for a nonlimiting list of natural and non-natural nucleotides and amino acids.

"ABC transporter" refers to orf2 or a protein encoded thereby from a strain of propionibacteria, mutants and polymorphisms found in nature, and variant forms thereof (e.g., mutants and polymorphisms not found in nature). The chemical structure of the ABC transporter may be a polymer of natural or non-natural nucleotides connected by natural or non-natural covalent linkages (i.e., polynucleotide) or a polymer of natural or non-natural amino acids connected by natural or non-natural covalent linkages (i.e., polypeptide). See Tables 1–4 of WIPO Standard ST.25 (1998) for a nonlimiting list of natural and non-natural nucleotides and amino acids.

"Mutants" are polynucleotides and polypeptides having at least one function that is more active or less active, an existing function that is changed or absent, a novel function that is not naturally present, or combinations thereof. "Polymorphisms" are polynucleotides and polypeptides that are genetically changed, but the changes do not necessarily have functional consequences. Bacteriocin and ABC transporter functions are described herein. The mutants and polymorphisms can be made by genetic engineering or chemical synthesis, but the latter is preferred for non-natural nucleotides, amino acids, or linkages.

"Oligonucleotides" and "oligopeptides" are short versions of polynucleotides and polypeptides (e.g., less than about 18, 24, 30 or 36 nucleotides or amino acids). They may be a fragment of a nucleotide or amino acid sequence described herein. They can be made by chemical synthesis, but they can be produced by chemical or enzymatic cleavage of longer polynucleotides or polypeptides. Biochemical techniques such as, for example, electrophoresis and/or reverse-phase high-performance liquid chromatography (HPLC) may be used to purify short products.

A bacteriocin or ABC transporter gene can be identified using stringent hybridization: e.g., 400 mM NaCl, 40 mM PIPES pH 6.4, 1 mM EDTA, 50° C. or 70° C. for an oligonucleotide; 500 mM NaHPO$_4$ pH 7.2, 7% sodium dodecyl sulfate (SDS), 1% bovine serum albumin (BSA), 1 mM EDTA, 45° C. or 65° C. for a polynucleotide of 50 bases or longer. A bacteriocin or ABC transporter protein can be identified using an antibody or other binding protein as a probe using stringent binding: e.g., 50 mM Tris-HCl pH 7.4, 500 mM NaCl, 0.05% TWEEN 20 surfactant, 1% BSA, room temperature. Washing conditions may be varied by adjusting the salt concentration and temperature such that the signal-to-noise ratio is sufficient for specific hybridization or binding. Isolation methods may be used to identify an unknown bacteriocin- or ABC transporter-related nucleic acid or protein using a probe which detects a known nucleic acid or protein, respectively. For example, a mixture of nucleic acids or proteins may be separated by one or more physical, chemical, and/or biological properties, and then the presence or absence of nucleic acid or protein related to the bacteriocin or ABC transporter may be detected by specific binding of the probe. The probe may also be used to detect the presence or absence of a known gene or protein, or to identify a previously unknown gene or protein. Blocking and washing conditions can be varied to obtain a nucleic acid hybridization or protein binding signal that is target specific and/or reduces the background.

An "isolated" product is at least partially purified from its microbial cell of origin or manufacturing source. For example, as compared to a lysate of the cell of origin, the isolated product may be at least 50%, 75%, 90%, 95% or 98% purified from other chemically-similar solutes (e.g., total nucleic acids for polynucleotides or total proteins for polypeptides). For a chemically-synthesized polymer of nucleotides or amino acids, purity is determined by comparison to prematurely terminated or blocked products and may, as a practical matter, be considered isolated without purification. Purification may be achieved by biochemical techniques such as, for example, cell fractionation, centrifugation, chromatography, electrophoresis, precipitation, specific binding, or combinations thereof. Generally, solvent (e.g., water) and functionally inert chemicals (e.g., salts and buffers) are disregarded when determining purity. Cloning is often used to isolate the desired product. Furthermore, as compared to the starting material (e.g., conditioned media or cell lysate), the isolated product may be at least 2 times, 5 times, 10 times, 25 times, or 100 times concentrated.

The meaning of "heterologous" depends on context. For example, ligation of heterologous nucleotide regions to form a chimera means that the regions are not found colinear in nature (e.g., propionibacteria-derived polynucleotide ligated to a non-propionibacteria transcriptional regulatory region). Another example is fusion of amino acid domains which are not found colinear in propionibacteria. Ligation of nucleotide regions or joining of amino acid domains, one derived from a bacterium and another derived from a bacteriophage, are heterologous because they are derived from different species. In a further example, transfection of a vector or expression construct into a heterologous host cell means that the vector or expression construct is not found in the cell's genome in nature. A "recombinant" product may result from ligating heterologous regions for a recombinant polynucleotide or fusing heterologous domains for a recombinant polypeptide. Recombination may be genetically engineered in vitro with purified enzymes or in vivo in a cell.

A nucleic acid (e.g., DNA or RNA, single- or double-stranded) that specifically hybridizes to bacteriocin or ABC transporter genes or transcripts thereof can be used as a probe or primer. Oligonucleotides or polynucleotides can be full length covering the entire gene or transcribed message (e.g., a recombinant clone in a phagemid, plasmid, bacteriophage, cosmid, or other vector), or a shorter length sequence which is unique to bacteriocin or ABC transporter genes or transcripts thereof but contains only a portion of same. A probe would stably bind its target to produce a hybridization signal specific for a bacteriocin or ABC transporter nucleic acid or protein, while a primer may bind its target less stably because repetitive cycles of polymerization or ligation will also produce a specific amplification signal. The nucleic acid may be at least 15, 30, 45, 60, 90, 120, 240, 360, 480, 600, 720, 1200, 2400, 5000, or 10K bases long (including intermediate ranges thereof).

Typically, a nucleotide sequence may show as little as 90% sequence identity, and more preferably at least 95% sequence identity compared to a coding region of SEQ ID NO:10, excluding any deletions or insertions which may be present, and still be considered related. Amino acid sequences are considered to be related with as little as 90% sequence identity compared to SEQ ID NO:11 or 12. But 95% or greater sequence identity is preferred and 98% or greater sequence identity is more preferred.

Conservative amino acid substitutions (e.g., pair Glu/Asp, Val/Ile, Ser/Thr, Arg/Lys or Gln/Asn) may also be considered when making comparisons because the chemical similarity of these pairs of amino acid residues would be expected to result in functional equivalency in many cases. Amino acid substitutions that are expected to conserve the biological function of the polypeptide would conserve chemical attributes of the substituted amino acid residues such as hydrophobicity, hydrophilicity, side-chain charge, or size. Functional equivalency or conservation of biological function may be evaluated by methods for structural determination and activity as described herein. Thus, amino acid sequences are considered to be related with as little as 90% sequence similarity between the two polypeptides; however, 95% or greater sequence similarity is preferred and 98% or greater sequence similarity is most preferred.

Use of complex mathematical algorithms is not required if sequences can be aligned without introducing too many gaps. But such algorithms are known in the art, and implemented using default parameters in a commercial software package. See Doolittle, *Of URFS and ORFS*, University Science Books, 1986; Gribskov & Devereux, *Sequence Analysis Primer*, Stockton Press, 1991; and references cited therein. Percentage identity between a pair of sequences may be calculated by the algorithm implemented in the BESTFIT computer program (Smith & Waterman, J. Mol. Biol., 147: 195–197,1981; Pearson, Genomics, 11:635–650, 1991). Another algorithm that calculates sequence divergence has been adapted for rapid database searching and implemented in the BLAST computer program (Altschul et al., Nucl. Acids Res., 25:3389–3402,1997). For example, at least 90% identity for a 100 amino acid or nucleotide sequence would allow ten or fewer deletions, insertions, or substitutions (each gap being represented as one or more deletions or insertions).

For expression in a heterologous host, the codons used in the native nucleotide sequences may be adapted for translation by adopting the codon preferences of the host. This would accommodate the translational machinery of the heterologous host without a substantial change in the chemical structure of the polypeptide.

Polypeptides of the invention and their variants (i.e., deletion, domain shuffling or duplication, insertion, substitution, or combinations thereof) are also useful for determining structure-function relationships (e.g., alanine scanning, internal deletion, N-terminal or C-terminal truncation, conservative or nonconservative amino acid substitution). For example, folding and processing of protein, secretion of the protein, inhibition by or resistance to bacteriocin, or combinations thereof. See Wells (Bio/Technology, 13:647–651, 1995) and U.S. Pat. No. 5,534,617. Directed evolution by random mutagenesis or gene shuffling may be used to acquire new and improved functions in accordance with selection criteria. Mutant and polymorphic polypeptides are encoded by suitable mutant and polymorphic polynucleotides. Structure-activity relationships of propionicin T1 and its immune factor may be studied using variant polypeptides produced by an expression construct transfected in a microbial cell with or without endogenous bacteriocin.

A nucleotide sequence of the invention can be used to produce a fusion polypeptide with at least one heterologous peptide domain (e.g., an affinity or epitope tag). An oligopeptide is useful for producing specific antibody and epitope mapping of a bacteriocin-specific antibody. A polypeptide may be at least 20, 25, 30, 35, 40, 45, 50, 60, 70, 80, 90, 100, 150, or more amino acids long (including intermediate ranges thereof). Oligopeptide may be conjugated to one affinity tag of a specific binding pair (e.g., anti body-digoxygenin/hapten/peptide, biotin-avidin/streptavidin, glutathione S transferase-glutathione, maltose binding protein-maltose, protein A or G/immunoglobulin, polyhistidine-nickel). Either a full-length polypeptide (e.g., SEQ ID NO:11 or 12) or a shorter fragment (e.g., N-terminal or C-terminal domain, mature protein) can be produced; optionally including a heterologous peptide domain. Polypeptide may be produced by manual or automated chemical synthesis, purified from natural sources, synthesized in transfected host cells, or combinations thereof.

A nucleotide sequence or a portion thereof can be used to monitor expression, to determine a sequence, to detect a variant, and/or to identify propionibacteria by genotype. The invention also provides hybridization probes and amplification primers (e.g., polymerase chain reaction, ligation chain reaction, other isothermal amplification reactions). A pair of such primers may be used for RT-PCR assays to quantitate bacteriocin transcript abundance within cells. Amplification primers may be between 15 and 30 nucleotides long (preferably about 25 nucleotides), anneal to either sense or antisense strand (preferably the pair will be complementary to each strand), and terminate at the 3' end anywhere within SEQ ID NO:10 or their complements. Therefore, this invention will be useful for development and utilization of bacteriocin primers and other oligonucleotides to quantitate cognate RNA and DNA within cells.

Binding of polynucleotides or polypeptides may take place in solution or on a substrate. The assay format may or may not require separation of bound from not bound. Detectable signals may be direct or indirect, attached to any part of a bound complex, measured competitively, amplified, or combinations thereof. A blocking or washing step may be interposed to improve sensitivity and/or specificity. Attachment of a polynucleotide or polypeptide, interacting protein, or binding molecule to a substrate before, after, or during binding results in capture of an unattached species. Such immobilization will be stably attached to the substrate under washing conditions. See U.S. Pat. Nos. 5,143,854 and 5,412,087.

Changes in gene expression may be manifested in the cell by affecting transcriptional initiation, transcript stability, translation of transcript into protein product, protein stability, glycoprotein processing, rate of folding or secretion, or combinations thereof. The gene, transcript, or polypeptide can also be assayed by techniques such as in vitro transcription, in vitro translation, Northern hybridization, nucleic acid hybridization, reverse transcription-polymerase chain reaction (RT-PCR), Southern hybridization, metabolic labeling, antibody binding, immunoprecipitation (IP), enzyme linked immunosorbent assay (ELISA), radioimmunoassay (RIA), fluorescent labeling, or histochemical staining.

A reporter or selectable marker gene whose product is easily assayed may be used for detection. Reporter genes include, for example, alkaline phosphatase, β-galactosidase (LacZ), chloramphenicol acetyltransferase (CAT), β-glucoronidase (GUS), luciferases (LUC), green and red fluorescent proteins (GFP and RFP, respectively), horseradish peroxidase (HRP), β-lactamase, and derivatives thereof (e.g., blue EBFP, cyan ECFP, yellow-green EYFP, destabilized GFP variants, stabilized GFP variants, or fusion variants sold as BD LIVING COLORS fluorescent proteins by Clontech). Reporter genes would use cognate substrates that are preferably assayed by a chromogen, fluorescent, or luminescent signal. Alternatively, assay product may be tagged with a heterologous epitope (e.g., FLAG, MYC, SV40 T antigen, glutathione transferase, polyhistidine, maltose binding protein) for which cognate antibodies or affinity resins are available. Examples of drugs for which selectable marker genes, which confer resistance, exist are ampicillin, hygromycin, kanamycin, puromycin, and tetracycline. A metabolic enzyme may be used as a selectable marker in an auxotroph.

A polynucleotide may be ligated to a linker oligonucleotide or conjugated to one member of a specific binding pair (e.g., antibody-digoxygenin/hapten/peptide epitope, biotin-avidin/streptavidin, glutathione S transferase or GST-glutathione, lectin-sugar, maltose binding protein-maltose, polyhistidine-nickel, protein A/G-immunoglobulin). The polynucleotide may be conjugated by ligation of a nucleotide sequence encoding the binding member. A polypeptide may be joined to one member of the specific binding pair by producing the fusion encoded by such a ligated or conjugated polynucleotide or, alternatively, by direct chemical linkage to a reactive moiety on the binding member by chemical cross-linking. Such polynucleotides and polypeptides may be used as an affinity reagent to identify, to isolate, and to detect interactions that involve specific binding of a transcript or protein product of the expression construct. Before or after affinity binding of the transcript or protein product, the member attached to the polynucleotide or polypeptide may be bound to its cognate binding member. This can produce a complex in solution or immobilized to a support. A protease recognition site (e.g., for enterokinase, Factor Xa, ICE, secretases, thrombin) may be included between adjoining domains to permit site-specific proteolysis that separates those domains and/or inactivates protein activity.

Probes and primers may be used to identify propionibacteria, as well as other bacteriocin or ABC transporter genes or variants thereof. For example, a microbe may be identified by genotyping, or its presence or absence may be detected. A probe or primer specific for a gene identified herein may be used to detect the presence or absence of the gene, and thereby infer that the source of the gene is present or absent, respectively. Genetic polymorphisms and mutations in the bacteriocin or ABC transporter gene may be specifically detected by positioning a potentially mismatched base(s) in the middle portion of a probe or the 3'-end of a primer to stabilize or to destabilize binding of the probe or primer to its target depending on whether the target's sequence at that position is complementary to the base or not, respectively.

Genetic polymorphisms and mutations may also be detected by a change in a restriction fragment length polymorphism (RFLP), nuclease-protected fragment (e.g., S1 nuclease, deoxyribonuclease I, ribonuclease A, H or T1), or amplified product. For complicated genetic fingerprints, identification of each component may not be needed because a side-by-side visual comparison may also detect differences (e.g., RAPD). Differences may also be detected by changes in the molecular weight (MW) or isoelectric point (pI) of the bacteriocin or ABC transporter by gel electrophoresis or isoelectric focusing, respectively.

A shuttle vector or expression construct is a recombinant nucleic acid that is deoxyribonucleic acid (DNA) and/or ribonucleic acid (RNA). Their physical form may be single-stranded or double-stranded; its topology may be linear or circular. They are preferably double-stranded deoxyribonucleic acids (dsDNA) or are converted into dsDNA after introduction into a cell (e.g., insertion of a single-stranded bacteriophage into a host genome as a prophage). The shuttle vector or expression construct may include one or more regions from a heterologous gene from a mammalian, insect, plant, fungal, bacterial, or viral source, as well as regions suitable for genetic manipulation (e.g., selectable marker, linker with multiple recognition sites for restriction endonucleases, promoter for in vitro transcription, primer annealing sites for in vitro replication). The shuttle vector or expression construct may be associated with protein and another nucleic acid in a carrier (e.g., packaged in a bacteriophage) or condensed with a chemical (e.g., cationic lipid or polymer) to target entry into a cell. Their choice and methods for introducing them into a microbe or cell is within the skill in the art.

A shuttle vector may be further comprised of an origin of replication (ori) which allows replication of the vector integrated in the host genome or as an autonomously replicating episome. Random or targeted integration into the host genome is more likely to ensure maintenance of the vector but episomes can be maintained by selective pressure or, alternatively, may be preferred for those applications in which the vector is present only transiently.

An expression construct may be further comprised of a regulatory region for gene expression (e.g., promoter, repressor or inducer binding site, upstream Shine-Dalgarno consensus sequences for initiation of translation, multiple stop codons which are downstream of the expression region to ensure termination of translation, cellular localization sequence). Different levels of transcription can be achieved using an agent with a regulatory system which responds to the agent (e.g., antibiotic, metabolite like a sugar, pH, temperature). Independent regulation of orf2 expression may increase the resistance of a microbe having the operon as compared to coregulated expression with pctA.

A nucleic acid may be both a shuttle vector and an expression construct.

A shuttle vector or an expression construct may be introduced into a microbe or cell by any transfection technique using, for example, one or more chemicals (e.g., calcium phosphate, lipids), biolistics, conjugation, electroporation, microinjection, or viral infection. The introduced nucleic acid may integrate into the host genome of the cell or be maintained as an episome.

A fungal (e.g., mold, yeast) or bacterial cell may be transfected. A homologous region from a gene can be used to direct integration to a particular genetic locus in the host genome and thereby regulate expression by native regulatory regions at the locus (e.g., homologous recombination of a promoterless reporter or selectable marker at the operon or a gene thereof) or ectopic copies of a bacteriocin or ABC transporter gene may be inserted. Polypeptide may also be produced in vitro with a cell extract or in vivo with a genetically manipulated cell.

Antibody specific for bacteriocin or ABC transporter are used for detection or inhibition of protein activity. Polyclonal or monoclonal antibodies may be prepared by immunizing animals (e.g., chicken, hamster, mouse, rat, rabbit, goat, horse) with antigen, and optionally affinity purified against the same or a related antigen. Antigen may be native protein, fragment made by proteolysis or genetic engineering, fusion protein, or in vitro translated or synthesized protein which includes at least one or more epitopes bound by the antibody. Antibody fragments may be prepared by proteolytic cleavage or genetic engineering; humanized antibody and single-chain antibody may be prepared by transplanting sequences from antigen binding domains of an antibody to framework molecules. Other binding molecules (e.g., agonists or antagonists of ligand-receptor binding) may be prepared by screening a combinatorial library for a member which specifically binds antigen (e.g., phage display library). Antigen may be a full-length protein encoded by the gene or fragment(s) thereof. The antibody may be specific for propionicin T1 or its immune factor, it may cross react with other bacteriocins or ABC transporters depending on how well conserved is the epitope recognized by the anti-body among different species. Immunoassay may be used to identify propionibacteria, or their presence or absence.

Bacteriocin-specific binding agents (e.g., polynucleotides, polypeptides) may be used diagnostically to detect bacteriocin nucleic acid or protein, or for treatment to confer bacteriocin activity (e.g., transcription, translation, processing, secretion). In particular, agents that affect expression of bacteriocin and bacteriocin interaction with a receptor (e.g., binding, signaling) are desirable.

ABC transporter-specific binding agents (e.g., polynucleotides, polypeptides) may be used diagnostically to detect ABC transporter nucleic acid or protein, or for treatment to inhibit bacteriocin activity (e.g., transcription, translation, processing, secretion). In particular, agents that affect expression of ABC transporter and ABC transporter interaction (e.g., binding, signaling) to a ligand are desirable.

The aforementioned binding agents may also be used for phenotyping microbes and identifying propionibacteria. Their presence or absence may be detected.

Infection by bacteria may be treated with the bacteriocin. The infection may be systemic or cutaneous and treated appropriately by systemic or topical administration of bacteriocin). The composition may be adapted for administration by an enteral or parenteral route; a cream, gel, or ointment form may be used for topical administration. The composition may include a carrier or vehicle to deliver bacteriocin to the site of infection. Optional active ingredients are other bacteriocins (e.g., propionicin PGL-1, jenseniin G), lantibiotics (e.g., nisin, pediocin PA1), antibiotics (e.g., tetracycline, erythromycin, clindamycin, meclocyclin, metronidazole, minocycline, doxycycline), and cell lysis agents (e.g., lysozyme). Optional inactive ingredients are drying agents (e.g., methyl or isopropyl alcohol), keratolytic agents (e.g., benzoyl peroxide, retinoic acid, salicylic acid), and preservatives (e.g., benzoic acid, butylated hydroxy anisole, parabens). Formulation of the composition may allow less antibiotic to be used and thereby reduce the disadvantages of side effects and antibiotic resistance. In particular, anaerobic infections (e.g., acne *vulgaris*) by cutaneous bacteria (e.g., *Propionibacterium acne, P. avidum, P. granulosum, P. lymphophilum*) may be treated.

Various bacteria mediate the conversion of milk into other food products. In particular, acid-forming bacteria are used in processes for making cheese, buttermilk, sour cream, yogurt, and other fermented dairy products. Controlling the growth of the bacteria used in producing such foods is important for ensuring edibility and flavor, as well as for preventing excessive curdling, the occurrence of undesirable secondary fermentations, and spoiling. Classical or dairy species include *P. acidipropionici, P. freudenreichii* ssp. *freudenreichii* and *shermanii, P. jensenii*, and *P. thoenii*. The growth of sensitive lactic acid bacteria and propionic acid bacteria may be inhibited by the bacteriocin; resistance is conferred by immunity factor. Either bacteriocin or microbes expressing the bacteriocin may be added before, during, or after fermentation. It may be added at one or more selected points in the fermentation or over an extended period; microbes may be induced or derepressed to express bacteriocin at one or more selected points in the fermentation or over an extended period. A dairy fermentation may contain milk, skim milk, whey, or culture media. It may be added in a starter primary or secondary culture, or directly to the food product by mixing or applying to the surface.

EXAMPLES

A collection of propionibacteria was screened for bacteriocin production and propionicin T1 was isolated from two strains of *Propionibacterium thoenii*. It showed no sequence similarity to other bacteriocins. Propionicin T1 was active against all strains of *Propionibacterium acidipropionici, Propionibacterium thoenii*, and *Propionibacterium jensenii* tested, and also against *Lactobacillus* sake NCDO 2714. But it showed no activity against *Propionibacterium freudenreichii*.

Propionicin T1 was purified and its N-terminal domain was determined by amino acid sequencing. The corresponding gene pctA was sequenced, and revealed that propionicin T1 is produced as a prebacteriocin of 96 amino acids with a typical sec-leader, which is processed to give a mature bacteriocin of 65 amino acids. An open reading frame encoding a protein of 424 amino acids was found 68 nucleotides downstream the stop codon of pctA. The N-terminal domain of this putative protein shows strong similarity with the ATP-binding cassette of prokaryotic and eukaryotic ABC transporters, and this protein may be involved in self-protection (i.e., resistance) against propionicin T1.

Bacterial strains and media. The bacterial strains used are shown in Table 1. The propionibacteria were propagated in sodium lactate broth (SLB) at 22° C. or 30° C. The propionibacteria used as indicator strains were propagated in SLB or M17 (Oxoid) with glucose (5 g/l) at 30° C. The indicator strain *Lactobacillus sake* NCDO 2714 was propagated in MRS (Difco) at 30° C.

Screening for antimicrobial activity. Colonies of strains of propionibacteria were grown on agar plates for 72 to 120 hr. A lawn of 5 ml GM17 soft agar containing 500 µl of a fresh culture of the indicator organisms was then poured over the plates. After incubation for 24 to 48 hr at 30° C., the colonies were examined for zones of growth inhibition.

Bacteriocin assay. Antimicrobial activity was determined by a microtiter plate assay (8). Each well of the microtiter plate contained 50 µl of twofold serial dilutions in SLB or GM17 of the bacteriocin samples, and 150 µl of a 100-fold-diluted fresh overnight culture of the indicator strain. The plates were incubated at 30° C. for 24 to 48 hr, and growth inhibition of the indicator organisms was measured spectrophotometrically at 620 nm with a microtiter plate reader. One bacteriocin unit (BU) was defined as the amount of bacteriocin that inhibited the growth of the indicator organism by 50% as compared with a control culture without bacteriocin.

Effect of proteinase K. Proteinase K (10 mg/ml) was spotted around colonies of potential bacteriocin producing bacteria. After an incubation period of one hour, soft agar with indicator strains was poured over the colonies. Lack of inhibition zones when

TABLE 1

Bacterial Strains and Species

| Indicator species | Strain[a] | Inhibition P. thoenii by 419[a,b] | Inhibition by P. thoenii LMG 2792[a,b] |
|---|---|---|---|
| *Propionibacterium acidipropionici* | ATCC 4965 | 5.0 | 3.0 |
| *Propionibacterium acidipropionici* | ATCC 4875 | 2.0 | 1.5 |

TABLE 1-continued

Bacterial Strains and Species

| Indicator species | Strain[a] | Inhibition P. thoenii by 419[a,b] | Inhibition by P. thoenii LMG 2792[a,b] |
|---|---|---|---|
| Propionibacterium jensenii | ATCC 4868 | 3.2 | 5.0 |
| Propionibacterium jensenii | ATCC 9614 | 4.0 | 3.5 |
| Propionibacterium jensenii | ATCC 4964 | 6.0 | 5.5 |
| Propionibacterium jensenii | ATCC 14072 | 1.5 | 0.3 |
| Propionibacterium jensenii | P 17 | 4.0 | 3.0 |
| Propionibacterium jensenii | P 52 | 3.2 | 2.0 |
| Propionibacterium thoenii | LMG 2792 | 3.0 | 2.0 |
| Propionibacterium thoenii | 419 | 3.0 | 2.0 |
| Propionibacterium thoenii | TL 221 | 4.0 | 2.0 |
| Propionibacterium thoenii | ATCC 4871 | 5.0 | 2.5 |
| Propionibacterium thoenii | ATCC 4872 | 3.5 | 2.5 |
| Lactobacillus sake | NCDO 2714 | 3.5 | 4.5 |

[a]Abbreviations: ATCC, American Type Culture Collection (Rockville, Md.); NCDO, National Collection of Food Bacteria (Reading, UK); LMG and P, our strain collection. *Propionibacterium thoenii* 419 comes from Environmental Bacteriology Culture Collection, University of the Orange Free State, South Africa. *Propionibacterium thoenii* TL 221 comes from L'Institut National de la Recherche Agronomique (INRA)
[b]Radius of inhibition zone in millimetres.

sensitive bacteria were used as indicators, indicated that the antimicrobial compound was of protein nature.

Bacteriocin purification. The bacteriocin was purified from 1-liter cultures of *Propionibacterium thoenii* 419. The culture was grown in SLB broth at 30° C. until early logarithmic phase (approximately 72 hr). The cells were removed from the supernatant by centrifugation at 12,000×g for 20 min at 4° C. The bacteriocin was precipitated from the culture supernatant by addition of ammonium sulphate to 40%. The sample was kept at 4° C. for at least one hour. After centrifugation at 12,000×g for 20 min, the pellet was dissolved in 50 ml water, and the pH of the sample was adjusted to pH 3.0 by addition of concentrated HCl. This solution was applied to a 3 ml SP-SEPHAROSE Fast-Flow cation-exchange column (Pharmacia LKB, Uppsala Sweden) equilibrated with 10 mM acetic acid. The column was washed with 10 ml of 30 mM sodium phosphate buffer (pH 6.0), 10 ml of 30 mM sodium phosphate buffer (pH 7.0) and 10 ml of 0.1 M NaCl before the bacteriocin was eluted in 9 ml of 0.3 M NaCl. The active fraction was further purified by reverse-phase chromatography (PepRPC™ HR5/5) using a FPLC (fast-performance liquid chromatography system; Pharmacia-LKB). The bacteriocin was eluted from the reverse-phase column with a linear 2-propanol gradient in 0.1% trifluoroacetic acid (TFA) at a flow rate of 0.5 ml min$^{-1}$. Fractions with high bacteriocin activity were then applied on a cation-exchange FPLC column (RESOURCE™S; Pharmacia-LKB) equilibrated with 5.0 mM sodium phosphate pH 6.0 in 50% methanol. The bacteriocin was eluted from this column with a linear gradient of 0–1.0 M NaCl in 5.0 mM sodium phosphate (pH 6.0) and 50% methanol buffer at a flow rate of 0.5 ml min$^{-1}$. The fractions with highest activity eluted from this column were then mixed and rechromatographed on the reverse-phase column to obtain pure bacteriocin.

The culture of *P. thoenii* LMG 2792 was grown at 22° C. until the late logarithmic phase (approximately 120 hr). The cells were removed from the supernatant by centrifugation at 12,000×g for 20 min at 4° C. The supernatant was adjusted to pH 4.0 with HCl, and applied to a 4 ml SP-SEPHAROSE Fast-Flow cation-exchange column (Pharmacia LKB) equilibrated with 10 mM acetic acid. Bacteriocin from this culture was then further purified by the same procedure as the bacteriocin from *P. thoenii* 419.

Effect of the bacteriocin on the viability of sensitive cells. Partially purified bacteriocin from *P. thoenii* 419 eluted in 0.3 M NaCl from an ion-exchange column was added in variable amounts to a 48 hr culture of *P. acidipropionici* grown in GM17, diluted 100-fold. Optical density at 620 nm and viable count (by dilution and plate counting) were determined at time intervals.

N-terminal amino acid sequencing. The N-terminal amino acid sequence was determined by automated Edman degradation using an Applied Biosystems 447A automatic sequence analyzer (Foster City, Calif.) with an on-line 120A amino acid phenylthiohydantoin analyzer as described by Cornwell et al. (2).

DNA sequence analysis. Total DNA from the bacteriocin-producing bacteria was obtained using ADVAMAX beads (Advanced Genetic Technologies Corp., Gaithersburg, Md.), following the procedure described by the manufacturer. Restriction enzymes, Taq-polymerase, and other DNA modifying enzymes were used as recommended by the manufacturers (Promega, Madison, Wis.; New England BioLabs Inc.; Hertfordshire, UK; Advanced Biotechnologies Ltd., London, UK).

PCR reactions were carried out in a DNA-Thermal Cycler (Perkin-Elmer Cetus, Norwalk, Conn.). The reactions (100 μl) were run with 2.5 units of Taq-polymerase (Advanced Biotechnologies Ltd.) and 100 pmol of each primer. The PCR conditions used for amplifying of small DNA fragments (>200 bp) included a hot start at 97° C. for 3 min, annealing at 55° C. for 30 sec, polymerization at 72° C. for 10 sec, and denaturation at 94° C. for 10 sec. The PCR condition used for primer walking included a hot start at 94° C. for 3 min; followed by 40 cycles of denaturation at 94° C. for 30 sec, annealing at 60° C. for 30 sec, and polymerization at 72° C. for 3 min.

PCR fragments were isolated by agarose gel electrophoresis, and extracted using WIZARD Plus SV Minipreps columns (Promega). The isolated PCR products were sequenced with the ABI PRISM Dye terminator Cycle Sequencing Ready reaction kit, and an ABI PRISM 377 DNA Sequencer (Perkin-Elmer).

Two degenerate primers 419P1 (5' GTN CCN GGN GGN TGY AC 3', SEQ ID NO:1) and 419P2 (5' TCN GGN GCR TTR TTR CA 3', SEQ ID NO:2) were designed from the amino acid sequence (N-terminal domain) of the bacteriocin obtained by Edman degradation, and used in PCR. New specific primers were designed from the sequence of the primary PCR product. Samples of total DNA were cut with different restriction enzymes (BamHI, SalI and SmaI), and ligated to the plasmid PBLUESCRIPT II SK+ (Stratagene, La Jolla, Calif.) cut with the same restriction enzymes. These ligation mixtures were used as templates in PCR reactions using combinations of bacteriocin specific primers (SEQ ID NOS:3–7) and the vector specific primer T7 (SEQ ID NO:8). New primers were constructed from the sequences of the PCR products obtained, and this procedure (primer walking) was repeated until the sequence shown in FIGS. 3A–3C was obtained.

TABLE 2

SEQ ID NOS:1–8

| PGR Primer | Sequence | Position |
|---|---|---|
| *Bacteriocin specific primer:* | | |
| 419P1 | 5' GTN CCN GGN GGN TGY AC 3' [a] | 385–401 |
| 419P2 | 5' TCN GGN GCR TTR TTR CA 3' | 475–491[b] |
| 419PA | 5' GTA CAC AAG AAG CAA TCG CGA 3' | 402–422 |
| 419PB | 5' CAG TCA AGT CGG ATT CGG AAC 3' | 456–476[b] |
| 419PC | 5' GTC TCA TGG GGT TCC CTT TTT 3' | 633–653[b] |
| 419PD | 5' CCA GGC CCG ATT CGC CCA CAG 3' | 1249–1269 |
| 419PE | 5' GCT GGT CGC GGC ACT GGC ATC 3' | 1759–1779 |
| T7 specific primer | 5' AAT ACG ACT CAC TAT AG 3' | |

[a] N: A, G, G or T, R: A or G, Y: C or T,
[b] Complementary strand

Analyses of DNA and protein sequences were performed using the OMIGA 1.1 DNA and Protein Sequence Analysis Software, (Oxford Molecular, UK). The signal peptide and cleavage site was identified with SignalP V1.1 (18).

Characterization of a Bacteriocin From Propionibacteria.

A collection of dairy propionibacteria was screened for antimicrobial activity. *Propionibacterium thoenii* strain 419 showed inhibitory activity against all strains tested of *Propionibacterium acidipropionici, Propionibacterium thoenii* and *Propionibacterium jensenii* when grown on agar plates (Table 1) Even the producer strain itself and *P. thoenii* LMG 2792 which produces the same bacteriocin, were sensitive against the antimicrobial activity produced by colonies of *P. thoenii* 419 (Table 1). Treatment with proteinase K inactivated the antimicrobial activity, indicating that the inhibitory compound was proteinaceous.

Ten strains of *Propionibacterium freudenreichii* were tested. None of them were inhibited by *P. thoenii* 419 in this overlay assay (results not shown). Strains of *Lactococcus, Lactobacillus, Enterococcus, Carnobacterium* and *Listeria* were also tested. None of these strains were inhibited except *Lactobacillus sake* NCDO 2714. The inhibitory activity was detected in liquid culture, and maximum antimicrobial activity was found in the early stationary growth phase (FIG. 1). Among the indicator strains tested *Propionibacterium acidipropionici* ATCC 4965 was one of the most sensitive on agar plates and in the microtiter plate assay, and was used as standard indicator.

The bacteriocin was isolated from *P. thoenii* 419 by a procedure involving ammonium sulphate precipitation and ion exchange and reverse phase chromatography. The new bacteriocin was named propionicin T1.

The first 38 amino acid residues of the N-terminal amino acid sequence of the bacteriocin were determined by Edman degradation. The following sequence was obtained: VPG-GCTYTRSNRDVIGTCKTGSGQFRIRLDCNNAPDKT (SEQ ID NO: 9). The same bacteriocin was also isolated and purified from stationary cultures of *Propionibacterium thoenii* LMG 2792. This strain showed the same inhibition spectrum as *P. thoenii* 419. The N-terminal amino acid sequence of the bacteriocin isolated from *P. thoenii* LMG 2792 was exactly identical with the sequence of the bacteriocin from *P. thoenii* 419. We assume that *P. thoenii* 419 and *P. thoenii* LMG 2792 are different strains of *Propionibacterium thoenii* because of morphological differences like color and slime production, and different growth optima. The two strains showed great differences with respect to bacteriocin production. While *P. thoenii* 419 produced the bacteriocin in late logarithmic growth phase, bacteriocin production in *P. thoenii* LMG 2792 could only be detected late in stationary phase (after 120 hr, results not shown). Bacteriocin production of *P. thoenii* LMG 2792 was observed at 22° C. but not at 30° C., while *P. thoenii* 419 produced the bacteriocin at 30° C.

Stability of propionicin T1. The stability of the peptide was tested, by exposing the bacteriocin (0.3 M NaCl eluate from the cation exchange column) to temperatures of 60° C. and 100° C. for 15 min and to pH 2.5 for one hour. No reduction in antimicrobial activity was observed. Thus, propionicin T1 is heat stable and acid stable. Freezing, thawing, and storage of the bacteriocin fraction at 4° C. or −20° C. up to six months or at room temperature for 24 hr, showed no effect on the bacteriocin activity.

Figure 2A:
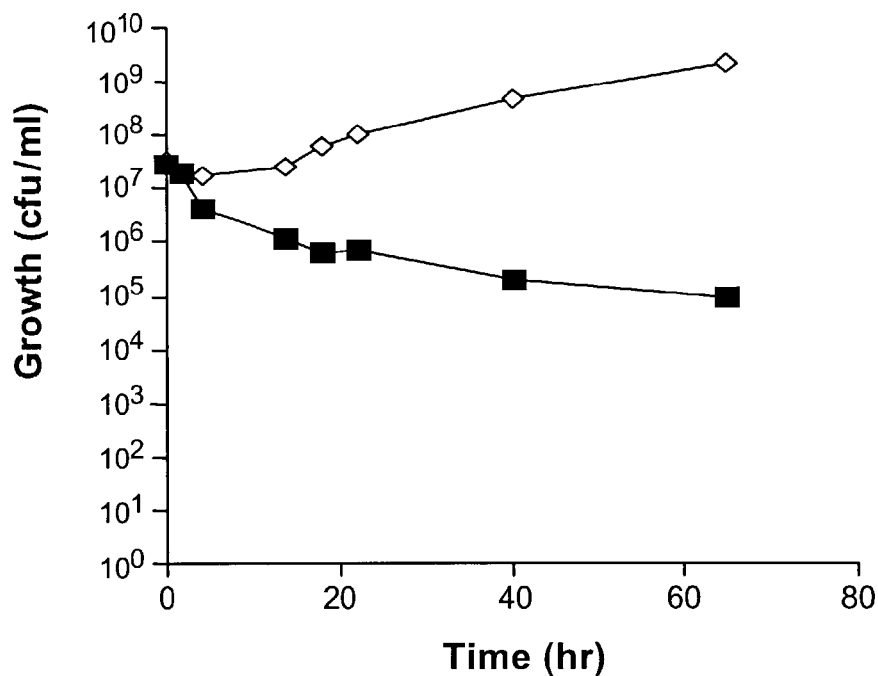
Figure 2B:
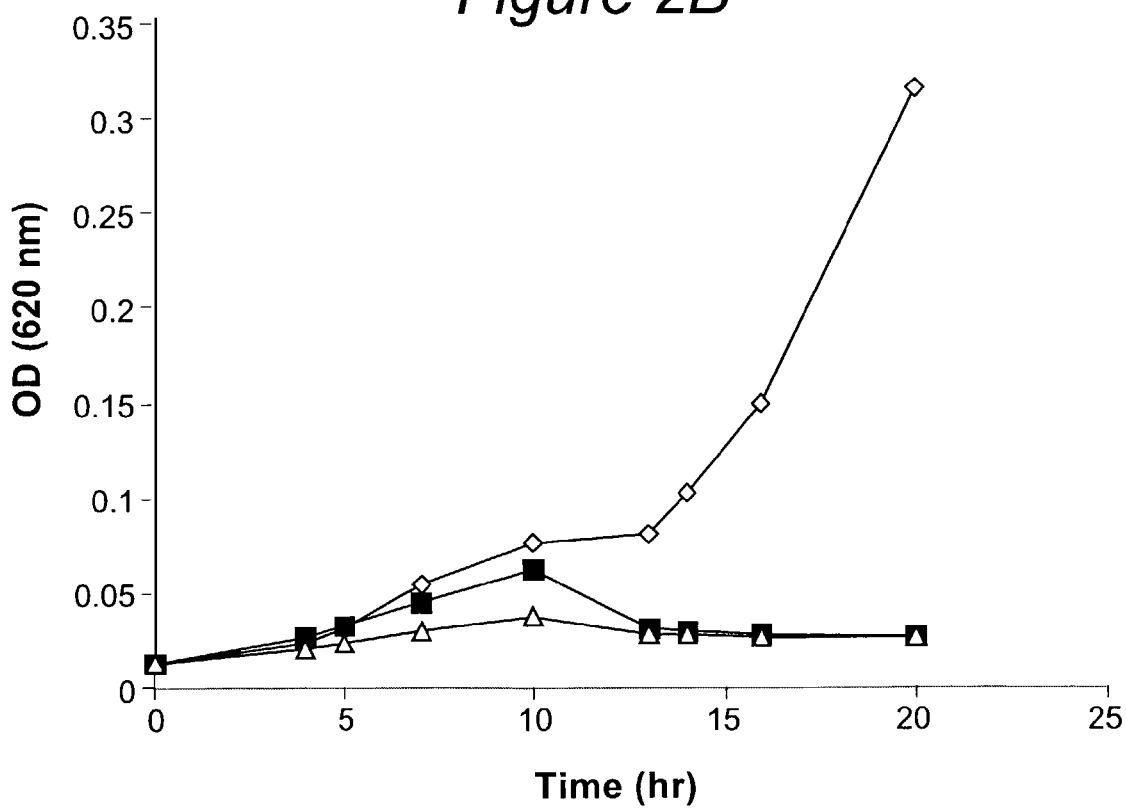

The effect of propionicin T1 on viability of sensitive cells. Several experiments were performed to show the effect of propionicin T1 on the viability of the indicator cells. Cultures of *P. acidipropionici* ATCC 4965 were exposed to different amounts of partially purified propionicin T1. FIGS. 2A and 2B show typical results from plate counting which demonstrated that propionicin T1 had a bactericidal effect on the indicator cells. A reduction in viable count was observed after 4 hr. More than 99% of the cells were killed after 40 hr (FIG. 2A). The same result was also obtained using 100 or 4000 BU/ml. Despite the reduction in cell number, bacteriocin treated cultures showed an increase in the optical density for several hours after addition of bacteriocin. This increase was followed by a decrease in optical density (FIG. 2B).

Genetic analyses of propionicin T1. Total DNA was isolated from *P. thoenii*LMG 2792. The sequence of the structural bacteriocin gene pctA was obtained by PCR using degenerate primers based on the N-terminal amino acid sequence, followed by a primer walking strategy. FIGS. 3A–3C show the DNA sequence of 2210 contiguous nucleotides (SEQ ID NO:10) including the open reading frame pctA. The DNA sequencing confirmed the results of the amino acid sequencing, and revealed that the bacteriocin is translated as a prebacteriocin of 96 amino acids (SEQ ID NO:11), which is processed to give a mature propionicin T1 of 65 amino acids (FIG. 3A). The prebacteriocin contains a typical sec-leader peptide (18), and this leader peptide is cleaved off immediately after the Ala-Met-Ala residues. The calculated molecular mass of the mature propionicin T1 was 7130.20 Da and the pI was calculated as 9.50. A putative promoter area was found upstream the start codon of the bacteriocin structural gene pctA (FIG. 3A). No amino acid or DNA sequence in various sequence databases showed significant similarity to the sequences presented here.

A second ORF, orf2, encoding a protein of 424 amino acids (SEQ ID NO:12) with a calculated molecular weight of 45163.95, was found 68 nucleotides downstream the stop codon of pctA (FIGS. 3A–3C). The ATG start codon is preceded seven nucleotides upstream by a potential ribosome-binding site (FIG. 3A). No potential promoter region was found upstream the start codon. The N-terminal domain of this putative protein shows strong similarity with the ATP-binding cassette of prokaryotic and eukaryotic ABC transporters (FIG. 4).

The ATP-hydrolyzing domains of ABC-transporters are characterized by three short sequence motifs in their primary structure: Walker A (GXXGXGKS/T where X can be varied, SEQ ID NO:19) and the linker peptide (LSGGQQ/R/KQR, SEQ ID NO:20) which precedes the Walker B motif (hhhhD where h stands for hydrophobic, SEQ ID NO:21) (27). These three motifs were found in the sequence encoded by orf2 (FIGS. 3A–3C).

Figure 5:
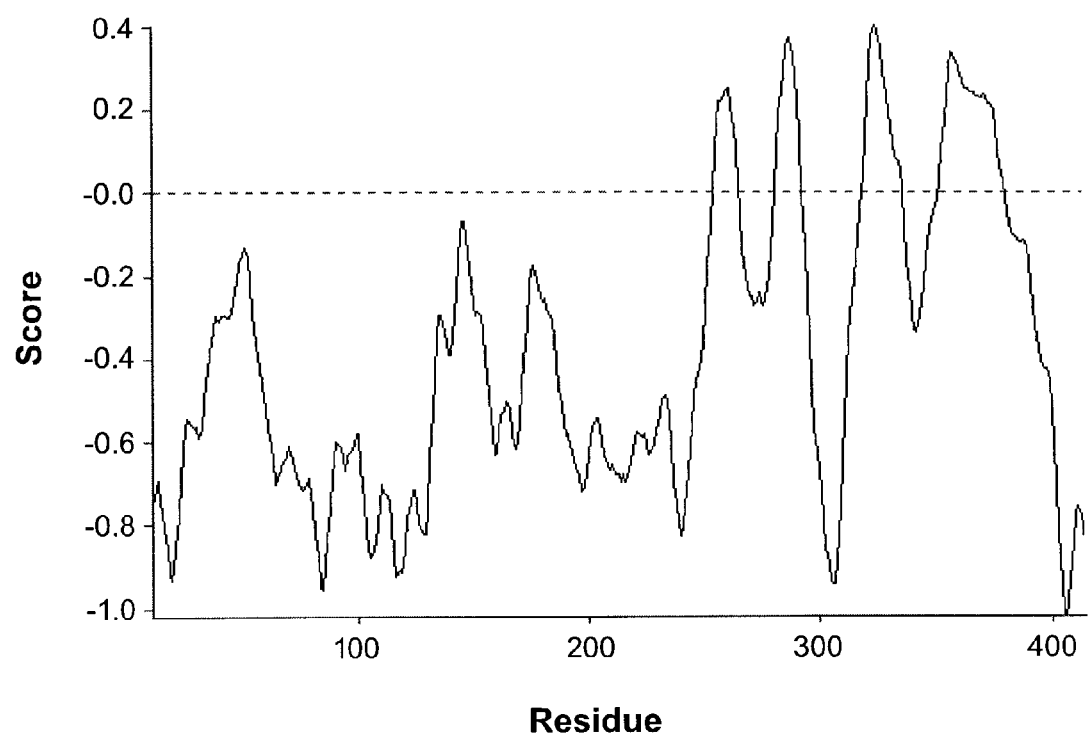
FIG. 5 shows a protein profile analysis of ORF2 which indicates the presence of a membrane-integral domain consisting of four potential transmembrane helices in the C-terminal domain of the protein.

Furthermore, the amino acid sequence indicates the presence of a membrane-integral domain consisting of four potential transmembrane helices in the C-terminal domain of the protein (FIG. 5).

Propionicin T1 is the first bacteriocin from propionibacteria that has been isolated and further characterized at the molecular level. Propionibacteria play an important role in the production and preservation of various dairy products, especially Swiss-type cheeses. Besides the production of propionic acid and other antagonistic compounds like acetic acid and carbon dioxide, bacteriocins from propionibacteria could contribute to this preservation. In addition to use in the food industry (e.g., affect fermentation, prevent spoilage, increase shelf life or storage term), bacteriocin may be used to treat infection by a sensitive pathogen.

The majority of bacteriocins characterized, have fairly narrow inhibition spectra, only killing bacteria closely related to the producer (10). Propionicin T1 falls into this category since it only inhibits a narrow group of propionibacteria. Classification studies based on 16S rDNA sequences have shown that the classical propionibacteria form two phylogenetic clusters, one containing *P. acidipropionici*, *P. thoenii*, and *P. jensenii*, and one cluster containing *P. freudenreichii* subspecies and the new species *P. cyclohexanicum* (4). Propionicin T1 seems to inhibit only the members in one of these two clusters of propionibacteria, since no strains of *P. freudenreichii* were inhibited by the bacteriocin. This may be of practical importance in cheese making. Propionicin T1 might be used to prevent the formation of red spots caused by pigment forming strains of *P. thoenii* and *P. jensenii*, a common problem in the production of Swiss-type cheeses, without harming the starter culture that contains strains of *P. freudenreichii*.

Sensitive bacteria were killed after exposure to the bacteriocin for several hours, demonstrating that propionicin T1 has a slow bactericidal mode of action. It was rather surprising to observe an increase in optical density in cultures with added bacteriocin. The first hours after bacteriocin addition this increase was almost identical to the increase in the control culture (FIG. 2B). Thus the optical density in the bacteriocin treated culture increased at the same time as the numbers of viable cells were reduced (FIGS. 2A and 2B). A similar phenomenon was observed for lactococcin 972 (15), a bacteriocin only active against lactococci. Addition of lactococcin 972 to sensitive cultures resulted in a sharp reduction in viable counts although the cells remained metabolically active. It was suggested that lactococcin 972 inhibited septum formation (15). Propionicin T1 may also interfere with the biosynthesis of essential macromolecules. Continued production of cellular compounds may explain the increase in optical density the first hours after bacteriocin addition.

The sequence of propionicin T1 shows no similarity to other bacteriocins. On the other hand, propionicin T1 has several features in common with most bacteriocins isolated from lactic acid bacteria they are relatively small (30–100 amino acids), thermostable, and cationic (17).

Like most bacteriocins from lactic acid bacteria propionicin T1 is synthesized as a precursor with a N-terminal leader peptide (10, 17). The deduced leader sequence of propionicin T1 conforms to be a typical signal peptide, as described by von Heijne (18), for proteins processed and secreted by the sec-dependent pathway (23). The signal peptides have a positively-charged amino terminus, a hydrophobic core and a specific cleavage region, features found in the leader sequence of propionicin T1.

An ORF encoding a peptide with the characteristics of an ABC transporter was found 68 nucleotides downstream the stop codon of the structural gene of propionicin T1. A potential ribosome binding site, but no obvious promoter region was found upstream of orf2. This gene can therefore be considered as a part of the pctA operon. The putative ABC transporter is not likely to be involved in the regular transport of propionicin T1 out of the cell, because as already mentioned the bacteriocin shows the features of proteins that are exported by the general secretory pathway.

Immunity factors protect the bacteria against self-toxicity, and the corresponding genes are usually located on the same operon as the structural bacteriocin genes (17). In most cases, the structural gene of the bacteriocin and the gene encoding the immunity protein are located adjacent to one another (1, 17). Several antibiotic resistance mechanisms involve ABC transporters (19). These systems export antibiotics out of the cells. It has been shown that dedicated ABC transporter systems also make an important contribution to producer protection against some bacteriocins. ABC transporters have so far been identified to be involved in self-protection of producers of nisin (26, 28), subtilin (12), epidermin (19, 21), and lacticin 481 (25).

Both producers of propionicin T1 were sensitive to their own bacteriocin in the overlay assay (Table 1). An explanation to this may be that the immunity factors are not constitutively expressed but connected to the production of the bacteriocin. Propionicin T1 is produced in late logarithmic stage by *P. thoenii* 419 and in stationary phase by *P. thoenii* LMG 2792. Apparently cells in early exponential growth phase are sensitive to the bacteriocin. This indicates that bacteriocin production and immunity are co-regulated.

The putative ABC-transporter encoded by orf2, may be involved in the immunity of the producer bacteria against propionicin T1 since this open reading frame probably is transcriptionally linked to the bacteriocin structural gene. The immunity could be mediated by active transport of bacteriocin molecules out of the producer cells, or by import and degradation of bacteriocin inside the cells.

REFERENCES

1. Allison & Klaenhammer (1996) Functional analysis of the gene encoding immunity to lactacin F, and its use as a *Lactobacillus*-specific, food-grade genetic marker. *Appl. Environ. Microbiol.* 62:4450–4460.
2. Cornwell et al. (1988) Evidence that the amyloid fibril protein in senile systemic amyloidosis is derived from normal prealbumin. *Biochem. Biophys. Res. Commun.* 154:648–653.
3. Daeschel (1989) Antimicrobial substances from lactic acid bacteria for use as food preservatives. *Food Technol.* 43:164–166.
4. Dasen et al. (1998) Classification and identification of propionibacteria based on ribosomal RNA genes and PCR. *Syst. Appl. Microbiol.* 21:251–259.

5. Delves et al. (1996) Applications of the bacteriocin nisin. *Antonie van Leeuwenhoek* 69:193–202.

6. González & Kunka (1987) Plasmid-associated bacteriocin production and sucrose fermentation in *Pediococcus acidilactici*. *Appl. Environ. Microbiol.* 53:2534–2538.

7. Grinstead & Barefoot (1992) Jenseniin G, a heat-stable bacteriocin produced by *Propionibacterium jensenii* P126. *Appl. Environ. Microbiol.* 58:215–220.

8. Holo et al. (1991) Lactococcin A, a new bacteriocin from *Lactococcus lactis* subsp. *cremoris*: isolation and characterization of the protein and its gene. *J. bacteriol.* 173:3879–3887.

9. Hsieh & Glatz (1996) Long-term storage stability of the bacteriocin propionicin PLG-1 produced by *Propionibacterium thoenii* and potential as a food preservative. *J. Food Prot.* 59:481–486.

10. Jack et al. (1995) Bacteriocins of gram-positive bacteria. *Microbiol. Rev.* 59:171–200.

11. Klaenhammer (1993) Genetics of bacteriocins produced by lactic acid bacteria. *FEMS Microbiol. Rev.* 12:39–86

12. Klein & Entian (1994) Genes involved in self-protection against the lantibiotic subtilin produced by *Bacillus subtilis* ATCC 6633. *Appl. Environ. Microbiol.* 60:2793–2801.

13. Lyon & Glatz (1991) Partial purification and characterization of a bacteriocin produced by *Propionibacterium thoenii*. *Appl. Environ. Microbiol.* 57:701–706.

14. Lyon & Glatz (1993) Isolation and purification of propionicin PLG-1, a bacteriocin produced by a strain of *Propionibacterium thoenii*. *Appl. Environ. Microbiol.* 59:83–88.

15. Martinez et al. (2000) *Lactococcin* 972, a bacteriocin that inhibits septum formation in lactococci. *Microbiology* 146:949–955.

16. Moll et al. 1999. Bacteriocins: mechanism of membrane insertion and pore formation. *Antonie van Leeuwenhoek* 76:185–198.

17. Nes et al. (1996) Biosynthesis of bacteriocins in lactic acid bacteria. *Antonie van Leeuwenhoek* 70:113–138.

18. Nielsen et al. (1997) Identification of procaryotic and eukaryotic signal peptides and prediction of their cleavage sites. *Protein Eng.* 10:1–6.

19. Otto et al. (1998) Producer self-protection against the lantibiotic epidermin by the ABC transporter EpiFEG of *Staphylococcus epidermis* Tü3298. *FEMS Microbiol. Lett.* 166:203–211.

20. Paik & Glatz (1995) Purification and partial amino acid sequence of propionicin PLG-1, a bacteriocin produced by *Propionibacterium thoenii* P127. *Lait* 75:367–377.

21. Peschel & Götz (1996) Analysis of the *Staphylococcus epidermidis* genes epiF, -E, and -G involved in epidermin immunity. *J. Bacteriol.* 178:531–536.

22. Pucci et al. (1988) Inhibition of *Listeria monocytogenes* by using bacteriocin PA-1 produced by *Pediococcus acidilactici* PAC 1.0. *Appl. Environ. Microbiol.* 54:2349–2353.

23. Pugsley (1993) The complete general secretory pathway in gram-negative bacteria. *Microbiol. Rev.* 57:50–108.

24. Ratnam et al. (1999) Partial purification and characterization of the bacteriocin produced by *Propionibacterium jensenii* B1264. *Lait* 79:125–136.

25. Rince et al. (1997) Characterization of the lactacin 481 operon: the *Lactococcus lactis* genes lctF, lctE, and lctG encode a putative ABC transporter involved in bacteriocin immunity. *Appl. Environ. Microbiol.* 63:4252–4260.

26. Saris et al. (1996) Immunity to lantibiotics. *Antonie Leeuwenhoek* 69:151–159.

27. Schneider & Hunke (1998) ATP-binding-cassette (ABC) transport systems: Functional and structural aspects of the ATP-hydrolyzing subunits/domains. *FEMS Microbiol. Rev.* 22:1–20.

28. Siegers & Entian (1995) Genes involved in immunity to the lantibiotic nisin produced by *Lactococcus lactis* 6F3. *Appl. Environ. Microbiol.* 61:1082–1089.

29. Stiles (1996) Biopreservation by lactic acid bacteria. *Antonie van Leeuwenhoek* 70:331–345.

30. de Vos et al. (1993) Properties of nisin Z and distribution of its gene, nisZ, in *Lactococcus lactis*. *Appl. Environ. Microbiol.* 59:213–218.

31. Weinbrenner et al. (1997) Inhibition of yogurt starter cultures by jensenim G, a *Propionibacterium bacteriocin*. *J. Dairy Sci.* 80:1246–1253.

Patents, patent applications, books, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. An isolated polypeptide comprising the amino acid sequence from position 32 to position 96 of SEQ ID NO:11, wherein the polypeptide has bacteriocin activity.

2. A fusion polypeptide comprising the amino acid sequence from position 32 to position 96 of SEQ ID NO:11 and a heterologous polypeptide, wherein the fusion polypeptide has bacteriocin activity.

3. A composition comprising the polypeptide according to claim 1.

4. A process for producing a bacteriocin polypeptide, comprising: (a) culturing the bacteriocin polypeptide of claim 1 in a microbe under conditions suitable to produce the polypeptide; and (b) isolating the bacteriocin polypeptide from the microbe.

5. A process for producing a bacteriocin polypeptide, comprising: (a) synthesizing the bacteriocin polypeptide of claim 1 in a reaction mixture under conditions suitable to produce the polypeptide; and (b) isolating the bacteriocin polypeptide from the reaction mixture.

* * * * *

SEQUENCE LISTING

<160> NUMBER OF SEQ ID NOS: 21

<210> SEQ ID NO 1
<211> LENGTH: 17
<212> TYPE: DNA
<213> ORGANISM: Artificial Sequence
<220> FEATURE:
<223> OTHER INFORMATION: primer 419P1
<220> FEATURE:
<221> NAME/KEY: misc_feature
<222> LOCATION: 3, 6, 9, 12
<223> OTHER INFORMATION: any nucleotide

<400> SEQUENCE: 1
gtnccnggng gntgyac                                                   17

<210> SEQ ID NO 2
<211> LENGTH: 17
<212> TYPE: DNA
<213> ORGANISM: Artificial Sequence
<220> FEATURE:
<223> OTHER INFORMATION: primer 419P2
<220> FEATURE:
<221> NAME/KEY: misc_feature
<222> LOCATION: 3, 6
<223> OTHER INFORMATION: any nucleotide

<400> SEQUENCE: 2
tcnggngcrt trttrca                                                   17

<210> SEQ ID NO 3
<211> LENGTH: 21
<212> TYPE: DNA
<213> ORGANISM: Artificial Sequence
<220> FEATURE:
<223> OTHER INFORMATION: primer 419PA

<400> SEQUENCE: 3
gtacacaaga agcaatcgcg a                                              21

<210> SEQ ID NO 4
<211> LENGTH: 21
<212> TYPE: DNA
<213> ORGANISM: Artificial Sequence
<220> FEATURE:
<223> OTHER INFORMATION: primer 419PB

<400> SEQUENCE: 4
cagtcaagtc ggattcggaa c                                              21

<210> SEQ ID NO 5
<211> LENGTH: 21
<212> TYPE: DNA
<213> ORGANISM: Artificial Sequence
<220> FEATURE:
<223> OTHER INFORMATION: primer 419PC

<400> SEQUENCE: 5
gtctcatggg gttccctttt t                                              21

<210> SEQ ID NO 6
<211> LENGTH: 21
<212> TYPE: DNA
<213> ORGANISM: Artificial Sequence
<220> FEATURE:
<223> OTHER INFORMATION: primer 419PD

```
<400> SEQUENCE: 6
ccaggcccga ttcgcccaca g                                              21

<210> SEQ ID NO 7
<211> LENGTH: 21
<212> TYPE: DNA
<213> ORGANISM: Artificial Sequence
<220> FEATURE:
<223> OTHER INFORMATION: primer 419PE

<400> SEQUENCE: 7
gctggtcgcg gcactggcat c                                              21

<210> SEQ ID NO 8
<211> LENGTH: 17
<212> TYPE: DNA
<213> ORGANISM: Artificial Sequence
<220> FEATURE:
<223> OTHER INFORMATION: T7 primer

<400> SEQUENCE: 8
aatacgactc actatag                                                   17

<210> SEQ ID NO 9
<211> LENGTH: 38
<212> TYPE: PRT
<213> ORGANISM: Propionibacterium thoenii

<400> SEQUENCE: 9

Val Pro Gly Gly Cys Thr Tyr Thr Arg Ser Asn Arg Asp Val Ile Gly
1               5                   10                  15

Thr Cys Lys Thr Gly Ser Gly Gln Phe Arg Ile Arg Leu Asp Cys Asn
            20                  25                  30

Asn Ala Pro Asp Lys Thr
        35

<210> SEQ ID NO 10
<211> LENGTH: 2210
<212> TYPE: DNA
<213> ORGANISM: Propionibacterium thoenii

<400> SEQUENCE: 10
tgacctgcgc cctgagccac tgatggcgaa tcgcactgat gccagcccg gccctcggca     60 tcaagatccc cgtctctaca cttcggcccg aacccctcag gaccttggtg gcgaacgtgg   120
ggaaggcgtg ccggacgccc tacccgatc gggtacacct gctacccgat cgggtagacc    180
ttcgcggaaa cgcttgcgtg agcacctcac cttccaccaa gatcgaaccc aagctcgagc   240
actcaaaccc attcggagaa tatcctctga ctgattagaa aggcccgctc gatgaagaag   300
accctcctgc gaagtggaac gatcgcactg gcgaccgcgg ctgcatttgg cgcatcattg   360
gcagccgccc catctgccat ggccgttcct ggtggttgca cgtacacaag aagcaatcgc   420
gacgtcatcg gtacctgcaa gactggaagc ggccagttcc gaatccgact tgactgcaac   480
aacgctccag acaaaacttc agtctgggcc aagcccaagg taatggtgtc ggttcactgt   540
cttgttggtc aaccgaggtc catctcgttc gagaccaagt gagtcgatag aactgatatc   600
ctcaatcctt ggaattcact gccctcaggg cgaagaaggg aaccccatga gactcgcggt   660
cgacggactg acggtgagat accggaagag ggtcgccgtc gacgcggtgt cctggcggct   720
tgatgagggc ttccacgcgc tgctgggccc caacggcgcg gggaagtcct cactgctgcg   780
```

```
cgcgatcgcc accctccagc cgacggtttc gggaaccgtt gagctggacg gacgcagcgg    840
aaccgagatc cgagcccatc ttggctactg ccccaggag aacctcggca ggtcccgatt    900
caccgttcgc gagcacctgg cctacatgtg ctggttgcac cgtatcccg actcccgggt    960 cccgtccgag gtggaccggg tcattgagct ggtggatctg gccgagcgtg ccgacgaccg    1020
gatctccgcc ctgtccggag ggatgcgccg cgggtcggc atcggttcgg cgctggtggg    1080
ccggccctca ctggtgatcc tcgacgaacc ctcggcaggg ctggacgtcg cccaacggga    1140
ggcgctgtcc tcggtcctgc aacgcgtctc ggccgaggcg atcaccatcg tgtcgaccca    1200
catcgtcgag gacgtcctgg accacgccga caccctgacc gtgatgaacc aggcccgatt    1260
cgcccacagc ggggccttcg acgagttcgc cggatcccgc gatctggagg ccgtgcgcat    1320
cgcgctacct ggagacggtg acaccgtgag gcacacggga gtcatgctgt gggcccgtca    1380
ccaccgggtg ggaccatcgg tcgcggtggc cgtcatcgcc tcggcggtcg tgcgcggact    1440
ggtgctcccc atcagctccg acggaagcga gatcgaggtg gccccactgt ggatcgccac    1500
cgtctgtgtc gtcccgttgc tgttcatgtt caccaccgag accgacaccg accgcaccgc    1560
cccacgatcc ctgacggccc gccggtgggc cctgctgggc atcgctgtcc tcacgagcgc    1620
ggtcatcgcc ctggcagcct tccccaccac catcggcgaa tggggactca tcgccacctg    1680
gcgcgacgcc gtcgccctgc tcgggctggg cctgctgagc ctggccgtcc tgccgccggc    1740
cgccatctgg gtggccccgc tggtcgcggc actggcatcg atgatgttca gctggccgct    1800
gcacccgggg actgtccctg ggactgtggg gagcgctgcg cgccgcggcc gacctgctgc    1860
tggacccggg cgtgaccgat ctgagtattc cgctgtgcct gctgatcagg gcggccggta    1920
gtcgtcttcc tcgtcaacgg cctgacatga accccacgcc caascgcccc cgatgggcga    1980
ccccaccacc gcaccgtgac gccccaccgc tccagtgccc gggccggcat caggagagcc    2040
tccctggccg tgccgatggc ctgcctggtc gccgtcgtct cggcctggcc gtgggtgacg    2100
tcactgtcgt ggtggggcgg cagccccagg ctcctgctgg ccggcgagat ccccgcctcg    2160
ttcttcatcg ccatacgctg cgcggtactg gccggcgtgg tgacaggcca              2210
```

<210> SEQ ID NO 11
<211> LENGTH: 96
<212> TYPE: PRT
<213> ORGANISM: Propionibacterium thoenii

<400> SEQUENCE: 11

```
Met Lys Lys Thr Leu Leu Arg Ser Gly Thr Ile Ala Leu Ala Thr Ala
1               5                   10                  15

Ala Ala Phe Gly Ala Ser Leu Ala Ala Ala Pro Ser Ala Met Ala Val
            20                  25                  30

Pro Gly Gly Cys Thr Tyr Thr Arg Ser Asn Arg Asp Val Ile Gly Thr
        35                  40                  45

Cys Lys Thr Gly Ser Gly Gln Phe Arg Ile Arg Leu Asp Cys Asn Asn
    50                  55                  60

Ala Pro Asp Lys Thr Ser Val Trp Ala Lys Pro Lys Val Met Val Ser
65                  70                  75                  80

Val His Cys Leu Val Gly Gln Pro Arg Ser Ile Ser Phe Glu Thr Lys
                85                  90                  95
```

<210> SEQ ID NO 12
<211> LENGTH: 424
<212> TYPE: PRT

<213> ORGANISM: Propionibacterium thoenii

<400> SEQUENCE: 12

| | | | | | | | | | | | | | |
|---|---|---|---|---|---|---|---|---|---|---|---|---|---|
| Met | Arg | Leu | Ala | Val | Asp | Gly | Leu | Thr | Val | Arg | Tyr | Arg | Lys | Arg | Val |
| 1 | | | | 5 | | | | | 10 | | | | | 15 | |

Met Arg Leu Ala Val Asp Gly Leu Thr Val Arg Tyr Arg Lys Arg Val
1               5                   10                  15

Ala Val Asp Ala Val Ser Trp Arg Leu Asp Glu Gly Phe His Ala Leu
                20                  25                  30

Leu Gly Pro Asn Gly Ala Gly Lys Ser Ser Leu Leu Arg Ala Ile Ala
            35                  40                  45

Thr Leu Gln Pro Thr Val Ser Gly Thr Val Glu Leu Asp Gly Arg Ser
    50                  55                  60

Gly Thr Glu Ile Arg Ala His Leu Gly Tyr Cys Pro Gln Glu Asn Leu
65                  70              75                      80

Gly Arg Ser Arg Phe Thr Val Arg Glu His Leu Ala Tyr Met Cys Trp
                85                  90                  95

Leu His Arg Ile Pro Asp Ser Arg Val Pro Ser Glu Val Asp Arg Val
            100                 105                 110

Ile Glu Leu Val Asp Leu Ala Glu Arg Ala Asp Asp Arg Ile Ser Ala
        115                 120                 125

Leu Ser Gly Gly Met Arg Arg Val Gly Ile Gly Ser Ala Leu Val
    130                 135                 140

Gly Arg Pro Ser Leu Val Ile Leu Asp Glu Pro Ser Ala Gly Leu Asp
145                 150                 155                 160

Val Ala Gln Arg Glu Ala Leu Ser Ser Val Leu Gln Arg Val Ser Ala
                165                 170                 175

Glu Ala Ile Thr Ile Val Ser Thr His Ile Val Glu Asp Val Leu Asp
            180                 185                 190

His Ala Asp Thr Leu Thr Val Met Asn Gln Ala Arg Phe Ala His Ser
        195                 200                 205

Gly Ala Phe Asp Glu Phe Ala Gly Ser Arg Asp Leu Glu Ala Val Arg
    210                 215                 220

Ile Ala Leu Pro Gly Asp Gly Asp Thr Val Arg His Thr Gly Val Met
225                 230                 235                 240

Leu Trp Ala Arg His His Arg Val Gly Pro Ser Val Ala Val Ala Val
                245                 250                 255

Ile Ala Ser Ala Val Val Arg Gly Leu Val Leu Pro Ile Ser Ser Asp
            260                 265                 270

Gly Ser Glu Ile Glu Val Ala Pro Leu Trp Ile Ala Thr Val Cys Val
        275                 280                 285

Val Pro Leu Leu Phe Met Phe Thr Thr Glu Thr Asp Thr Asp Arg Thr
    290                 295                 300

Ala Pro Arg Ser Leu Thr Ala Arg Arg Trp Ala Leu Leu Gly Ile Ala
305                 310                 315                 320

Val Leu Thr Ser Ala Val Ile Ala Leu Ala Ala Phe Pro Thr Thr Ile
                325                 330                 335

Gly Glu Trp Gly Leu Ile Ala Thr Trp Arg Asp Ala Val Ala Leu Leu
            340                 345                 350

Gly Leu Gly Leu Leu Ser Leu Ala Val Leu Pro Pro Ala Ala Ile Trp
        355                 360                 365

Val Ala Pro Leu Val Ala Ala Leu Ala Ser Met Met Phe Ser Trp Pro
    370                 375                 380

Leu His Pro Gly Thr Val Pro Gly Thr Val Gly Ser Ala Ala Arg Arg
385                 390                 395                 400

-continued

```
Gly Arg Pro Ala Ala Gly Pro Gly Arg Asp Arg Ser Glu Tyr Ser Ala
                405                 410                 415
Val Pro Ala Asp Gln Gly Gly Arg
            420

<210> SEQ ID NO 13
<211> LENGTH: 238
<212> TYPE: PRT
<213> ORGANISM: Artificial Sequence
<220> FEATURE:
<223> OTHER INFORMATION: ABC/1-429

<400> SEQUENCE: 13

Ile Glu Val Glu Ser Val Ser Lys Ser Phe Gly Arg Ile Arg Ala Leu
1               5                   10                  15
Asp Asn Leu Ser Phe Ser Val Ala Glu Gly Leu Met Gly Ile Ile
            20                  25                  30
Gly His Asn Gly Ala Gly Lys Thr Thr Ala Ile Arg Ile Ile Ala Gly
            35                  40                  45
Ile Leu His Pro Asp Ser Gly Thr Val Arg Val Gly Gly His Asp Val
        50                  55                  60
Thr Glu Asp Pro Leu Ser Val Lys Ser Met Ile Gly Tyr Leu Pro Glu
65                  70                  75                  80
Glu Pro Asn Leu Tyr Glu Arg Phe Arg Ala Gly Asp Leu Leu Arg Tyr
                85                  90                  95
Phe Gly Glu Leu Tyr Gly Val Pro Arg Asp Val Leu Asp Asp Arg Ile
                100                 105                 110
Ala Glu Leu Leu Glu Leu Val Gly Met Thr Asp Arg Ala Met Asp Pro
            115                 120                 125
Ile Asn Thr Phe Ser Lys Gly Leu Arg Gln Arg Ile Gly Ile Ala Arg
        130                 135                 140
Ala Leu Ile His Asp Pro Pro Ile Ile Phe Asp Glu Pro Thr Met
145                 150                 155                 160
Gly Leu Asp Pro Ala Thr Ala Phe Ser Ile Arg Glu Phe Ile Arg Asp
                165                 170                 175
Leu Lys Gly Ser Lys Thr Met Ile Leu Cys Thr His Tyr Met Glu Glu
                180                 185                 190
Ala Glu Tyr Leu Cys Asp Arg Val Ala Ile Ile Asn Gln Gly Arg Ile
            195                 200                 205
Leu Asp Ile Gly Thr Pro Asp Glu Leu Lys Ser Lys Ile Arg Gly Asp
        210                 215                 220
Leu Val Leu Glu Val Lys Val Arg Asp Ile Ser Ser Val Gly
225                 230                 235

<210> SEQ ID NO 14
<211> LENGTH: 211
<212> TYPE: PRT
<213> ORGANISM: Artificial Sequence
<220> FEATURE:
<223> OTHER INFORMATION: Homologous/1-429

<400> SEQUENCE: 14

Leu Ser Ile Glu Ser Leu Cys Lys Ser Tyr Arg His His Glu Ala Val
1               5                   10                  15
Lys Asn Val Ser Phe His Val Asn Glu Asn Glu Cys Val Ala Leu Leu
            20                  25                  30
Gly Pro Asn Gly Ala Gly Lys Thr Thr Thr Leu Gln Met Leu Ala Gly
            35                  40                  45
```

```
Leu Leu Ser Pro Thr Ser Gly Thr Ile Lys Leu Leu Gly Glu Lys Lys
         50                  55                  60

Leu Asp Arg Arg Leu Ile Gly Tyr Leu Pro Gln Tyr Pro Ala Phe Tyr
 65                  70                  75                  80

Ser Trp Met Thr Ala Asn Glu Phe Leu Thr Phe Ala Gly Arg Leu Ser
                 85                  90                  95

Gly Leu Ser Lys Arg Lys Cys Gln Glu Lys Ile Gly Glu Met Leu Glu
            100                 105                 110

Phe Val Gly Leu His Glu Ala Ala His Lys Arg Ile Gly Gly Tyr Ser
        115                 120                 125

Gly Gly Met Lys Gln Arg Leu Gly Leu Ala Gln Ala Leu Leu His Lys
    130                 135                 140

Pro Lys Phe Leu Ile Leu Asp Glu Pro Val Ser Ala Leu Asp Pro Thr
145                 150                 155                 160

Gly Arg Phe Glu Val Leu Asp Met Met Arg Glu Leu Lys Lys His Met
                165                 170                 175

Ala Val Leu Phe Ser Thr His Val Leu His Asp Ala Glu Gln Val Cys
            180                 185                 190

Asp Gln Val Val Ile Met Lys Asn Gly Glu Ile Ser Trp Lys Gly Glu
        195                 200                 205

Leu Gln Glu
    210

<210> SEQ ID NO 15
<211> LENGTH: 192
<212> TYPE: PRT
<213> ORGANISM: Artificial Sequence
<220> FEATURE:
<223> OTHER INFORMATION: Putative/1-429

<400> SEQUENCE: 15

Leu Ala Leu Asp Cys Leu Asn Leu Arg Leu Tyr Glu Gly Gln Ile Thr
  1               5                  10                  15

Gly Leu Leu Gly His Asn Gly Ala Gly Lys Thr Thr Thr Met Ser Ile
             20                  25                  30

Leu Cys Gly Leu Tyr Ala Pro Ser Gly Thr Ala Lys Ile Tyr Gln
         35                  40                  45

Arg Asp Ile Arg Thr Asp Leu Arg Arg Val Arg Asp Val Leu Gly Ile
 50                  55                  60

Cys Pro Gln His Asn Val Leu Phe Ser His Leu Thr Val Ser Glu Gln
 65                  70                  75                  80

Leu Arg Leu Phe Ala Ala Leu Lys Gly Val Pro Asp Ser Glu Leu Thr
                 85                  90                  95

Ser Gln Val Asp Glu Ile Leu Ala Ser Val Ser Leu Thr Glu Lys Ala
            100                 105                 110

Asn Lys Leu Ala Ser Thr Leu Ser Gly Gly Met Lys Arg Arg Leu Cys
        115                 120                 125

Ile Gly Ile Ala Phe Ile Gly Gly Ser Arg Phe Val Ile Leu Asp Glu
    130                 135                 140

Pro Thr Ala Gly Val Asp Val Thr Ala Arg Lys Asp Ile Trp Lys Leu
145                 150                 155                 160

Leu Gln Arg Asn Lys Glu Gly Arg Thr Ile Leu Leu Ser Thr His His
                165                 170                 175

Met Asp Glu Ala Asp Val Leu Ser Asp Arg Ile Ala Ile Leu Ser Gln
            180                 185                 190
```

```
<210> SEQ ID NO 16
<211> LENGTH: 227
<212> TYPE: PRT
<213> ORGANISM: Artificial Sequence
<220> FEATURE:
<223> OTHER INFORMATION: putative/1-429

<400> SEQUENCE: 16

Ile Thr Leu Asp Arg Leu Thr Lys Arg Tyr Gly Asp Lys Thr Ala Val
  1               5                  10                  15

Ser Asp Leu Ser Phe Glu Ile Asn Pro Gly Lys Val Thr Gly Phe Leu
             20                  25                  30

Gly Pro Asn Gly Ala Gly Lys Ser Thr Thr Met Arg Met Ile Val Gly
         35                  40                  45

Leu Asp Ala Pro Thr Ser Gly Arg Ala Leu Val Gly Gly Lys Arg Tyr
     50                  55                  60

Glu Glu Leu Arg His Pro Leu Arg Glu Val Gly Ala Leu Leu Asp Ala
 65                  70                  75                  80

Arg Ala Gly His Pro Gly Arg Ser Ala Arg His His Leu Leu Gly Leu
                 85                  90                  95

Ala Arg Ser Asn Gly Ile Pro Ala Ser Arg Val Gly Glu Val Leu Gln
            100                 105                 110

Thr Val Gly Leu Ser Glu Val Ala Asn Lys Arg Ile Gly Ser Phe Ser
        115                 120                 125

Leu Gly Met Gly Gln Arg Leu Gly Ile Ala Ala Leu Leu Gly Asp
    130                 135                 140

Pro Lys Val Leu Leu Phe Asp Glu Pro Val Asn Gly Leu Asp Pro Asp
145                 150                 155                 160

Gly Val Arg Trp Val Arg Glu Leu Met Arg Ser Leu Ala Ala Glu Gly
                165                 170                 175

Arg Thr Ile Phe Val Ser Ser His Leu Met Ser Glu Met Gln Glu Thr
            180                 185                 190

Ala Asp His Leu Leu Val Ile Gly Arg Gly Lys Ile Ile Ala Asp Ala
        195                 200                 205

Pro Ile Glu Glu Val Ile Ala Gly Ser Ser Leu Thr Ala Val Arg Val
    210                 215                 220

Arg Thr Pro
225

<210> SEQ ID NO 17
<211> LENGTH: 203
<212> TYPE: PRT
<213> ORGANISM: Artificial Sequence
<220> FEATURE:
<223> OTHER INFORMATION: ABC-C/1-429

<400> SEQUENCE: 17

Lys Asp Arg Ala Ala Val Arg Asp Leu Asn Leu Asn Leu Tyr Glu Gly
  1               5                  10                  15

Gln Ile Thr Val Leu Leu Gly His Asn Gly Ala Gly Lys Thr Thr Thr
             20                  25                  30

Leu Ser Met Leu Thr Gly Leu Phe Pro Pro Thr Ser Gly Arg Ala Tyr
         35                  40                  45

Ile Ser Gly Tyr Glu Ile Ser Gln Asp Met Val Gln Ile Arg Lys Ser
     50                  55                  60

Leu Gly Leu Cys Pro Gln His Asp Ile Leu Phe Asp Asn Leu Thr Val
```

-continued

```
                65                  70                  75                  80
Ala Glu His Leu Tyr Phe Tyr Ala Gln Leu Lys Gly Leu Ser Arg Gln
                    85                  90                  95

Lys Cys Pro Glu Glu Val Lys Gln Met Leu His Ile Ile Gly Leu Glu
                100                 105                 110

Asp Lys Trp Asn Ser Arg Ser Arg Phe Leu Ser Gly Met Arg Arg
                115                 120                 125

Lys Leu Ser Ile Gly Ile Ala Leu Ile Ala Gly Ser Lys Val Leu Ile
            130                 135                 140

Leu Asp Glu Pro Thr Ser Gly Met Asp Ala Ile Ser Arg Arg Ala Ile
145                 150                 155                 160

Trp Asp Leu Leu Gln Arg Gln Lys Ser Asp Arg Thr Ile Val Leu Thr
                165                 170                 175

Thr His Phe Met Asp Glu Ala Asp Leu Leu Gly Asp Arg Ile Ala Ile
                180                 185                 190

Met Ala Lys Gly Glu Leu Gln Cys Cys Gly Ser
            195                 200
```

<210> SEQ ID NO 18
<211> LENGTH: 235
<212> TYPE: PRT
<213> ORGANISM: Artificial Sequence
<220> FEATURE:
<223> OTHER INFORMATION: ORF2/1-429

<400> SEQUENCE: 18

```
Met Arg Leu Ala Val Asp Gly Leu Thr Val Arg Tyr Arg Lys Arg Val
1               5                   10                  15

Ala Val Asp Ala Val Ser Trp Arg Leu Asp Glu Gly Phe His Ala Leu
                20                  25                  30

Leu Gly Pro Asn Gly Ala Gly Lys Ser Ser Leu Leu Arg Ala Ile Ala
            35                  40                  45

Thr Leu Gln Pro Thr Val Ser Gly Thr Val Glu Leu Asp Gly Arg Ser
        50                  55                  60

Gly Thr Glu Ile Arg Ala His Leu Gly Tyr Cys Pro Gln Glu Asn Leu
65                  70                  75                  80

Gly Arg Ser Arg Phe Thr Val Arg Glu His Leu Ala Tyr Met Cys Trp
                85                  90                  95

Leu His Arg Ile Pro Asp Ser Arg Val Pro Ser Glu Val Asp Arg Val
                100                 105                 110

Ile Glu Leu Val Asp Leu Ala Glu Arg Ala Asp Asp Arg Ile Ser Ala
            115                 120                 125

Leu Ser Gly Gly Met Arg Arg Arg Val Gly Ile Gly Ser Ala Leu Val
        130                 135                 140

Gly Arg Pro Ser Leu Val Ile Leu Asp Glu Pro Ser Ala Gly Leu Asp
145                 150                 155                 160

Val Ala Gln Arg Glu Ala Leu Ser Ser Val Leu Gln Arg Val Ser Ala
                165                 170                 175

Glu Ala Ile Thr Ile Val Ser Thr His Ile Val Glu Asp Val Leu Asp
                180                 185                 190

His Ala Asp Thr Leu Thr Val Met Asn Gln Ala Arg Phe Ala His Ser
            195                 200                 205

Gly Ala Phe Asp Glu Phe Ala Gly Ser Arg Asp Leu Glu Ala Val Arg
        210                 215                 220

Ile Ala Leu Pro Gly Asp Gly Asp Thr Val Arg
```

```
225                 230                 235

<210> SEQ ID NO 19
<211> LENGTH: 8
<212> TYPE: PRT
<213> ORGANISM: Artificial Sequence
<220> FEATURE:
<223> OTHER INFORMATION: Walker A
<220> FEATURE:
<221> NAME/KEY: MISC_FEATURE
<222> LOCATION: 2, 3, 5, 8
<223> OTHER INFORMATION: any amino acid

<400> SEQUENCE: 19

Gly Xaa Xaa Gly Xaa Gly Lys Xaa
1               5

<210> SEQ ID NO 20
<211> LENGTH: 8
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: 6
<223> OTHER INFORMATION: glutamine or arginine or lysine

<400> SEQUENCE: 20

Leu Ser Gly Gly Gln Xaa Gln Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Walker B
<220> FEATURE:
<221> NAME/KEY: MISC_FEATURE
<222> LOCATION: 1, 2, 3, 4
<223> OTHER INFORMATION: hydrophobic amino acid

<400> SEQUENCE: 21

Xaa Xaa Xaa Xaa Asp
1               5
```